United States Patent
Neel et al.

(10) Patent No.: US 7,819,161 B2
(45) Date of Patent: Oct. 26, 2010

(54) SYSTEMS AND METHODS FOR BLOOD GLUCOSE SENSING

(75) Inventors: Gary T. Neel, Weston, FL (US); Douglas E. Bell, Coral Springs, FL (US); T. Philip Wong, Coral Springs, FL (US); Houston F. Voss, Fort Lauderdale, FL (US); Allan Javier Caban, Lakeworth, FL (US); David K. Boehm, Lauderhill, FL (US)

(73) Assignee: Nipro Diagnostics, Inc., Ft. Lauderdale, FL (US)

( * ) Notice: Subject to any disclaimer, the term of this patent is extended or adjusted under 35 U.S.C. 154(b) by 1021 days.

(21) Appl. No.: 11/590,854

(22) Filed: Nov. 1, 2006

(65) Prior Publication Data
US 2007/0089987 A1   Apr. 26, 2007

Related U.S. Application Data

(60) Continuation of application No. 10/706,458, filed on Nov. 12, 2003, now abandoned, which is a division of application No. 10/286,648, filed on Nov. 1, 2002, now Pat. No. 6,743,635.

(60) Provisional application No. 60/375,017, filed on Apr. 25, 2002, provisional application No. 60/375,019, filed on Apr. 25, 2002, provisional application No. 60/375,020, filed on Apr. 25, 2002, provisional application No. 60/375,054, filed on Apr. 25, 2002.

(51) Int. Cl.
*G01N 27/327* (2006.01)
(52) U.S. Cl. .............. 156/510; 204/403.01; 204/403.02
(58) Field of Classification Search ............ 204/403.01, 204/403.02, 403.04; 205/777.5, 792; 156/510
See application file for complete search history.

(56) References Cited

U.S. PATENT DOCUMENTS 4,714,874 A   12/1987   Morris et al.

(Continued)

FOREIGN PATENT DOCUMENTS

EP   0 170 375   5/1990

(Continued)

OTHER PUBLICATIONS

Renda et al., "A Practical Look at Self-Monitoring of Blood Glucose," *Insulin*, vol. 1, No. 4, pp. 141-147, 2006.

(Continued)

*Primary Examiner*—Kaj K Olsen
(74) *Attorney, Agent, or Firm*—Finnegan, Henderson, Farabow, Garrett & Dunner, L.L.P.

(57) ABSTRACT

A system for measuring a glucose level in a blood sample includes a test strip and a meter. The test strip includes a sample chamber, a working electrode, a counter electrode, fill-detect electrodes, and an auto-on conductor. A reagent layer is disposed in the sample chamber. The auto-on conductor causes the meter to wake up and perform a test strip sequence when the test strip is inserted in the meter. The meter uses the working and counter electrodes to initially detect the blood sample in the sample chamber and uses the fill-detect electrodes to check that the blood sample has mixed with the reagent layer. The meter applies an assay voltage between the working and counter electrodes and measures the resulting current. The meter calculates the glucose level based on the measured current and calibration data saved in memory from a removable data storage device associated with the test strip.

35 Claims, 19 Drawing Sheets

U.S. PATENT DOCUMENTS

| | | | |
|---|---|---|---|
| 4,841,981 | A | 6/1989 | Tanabe et al. |
| 4,894,137 | A | 1/1990 | Takizawa et al. |
| 4,900,424 | A | 2/1990 | Birth et al. |
| 5,053,199 | A | 10/1991 | Keiser et al. |
| 5,120,420 | A | 6/1992 | Nankia et al. |
| 5,128,015 | A | 7/1992 | Szuminsky et al. |
| 5,141,868 | A | 8/1992 | Shanks et al. |
| 5,264,103 | A | 11/1993 | Yoshioka et al. |
| 5,264,106 | A | 11/1993 | McAleer et al. |
| 5,266,179 | A | 11/1993 | Nankai et al. |
| 5,288,636 | A | 2/1994 | Pollmann et al. |
| 5,320,732 | A | 6/1994 | Nankai et al. |
| 5,352,351 | A | 10/1994 | White et al. |
| 5,366,609 | A | 11/1994 | White et al. |
| 5,395,504 | A | 3/1995 | Saurer et al. |
| 5,405,511 | A | 4/1995 | White et al. |
| 5,437,999 | A | 8/1995 | Diebold et al. |
| 5,438,271 | A | 8/1995 | White et al. |
| 5,494,562 | A | 2/1996 | Maley et al. |
| 5,502,396 | A | 3/1996 | Desarzens et al. |
| 5,508,171 | A | 4/1996 | Walling et al. |
| 5,526,120 | A | 6/1996 | Jina et al. |
| 5,575,895 | A | 11/1996 | Ikeda et al. |
| 5,582,697 | A | 12/1996 | Ikeda et al. |
| 5,589,045 | A | 12/1996 | Hyodo |
| 5,628,890 | A | 5/1997 | Carter et al. |
| 5,650,062 | A | 7/1997 | Ikeda et al. |
| 5,682,884 | A | 11/1997 | Hill et al. |
| 5,708,247 | A | 1/1998 | McAleer et al. |
| 5,720,862 | A | 2/1998 | Hamamoto et al. |
| 5,728,074 | A | 3/1998 | Castellano et al. |
| 5,762,770 | A | 6/1998 | Pritchard et al. |
| 5,820,551 | A | 10/1998 | Hill et al. |
| 5,837,546 | A | 11/1998 | Allen et al. |
| 5,925,021 | A | 7/1999 | Castellano et al. |
| RE36,268 | E | 8/1999 | Szuminsky et al. |
| 5,951,836 | A | 9/1999 | McAleer et al. |
| 5,989,917 | A | 11/1999 | McAleer et al. |
| 6,071,391 | A | 6/2000 | Gotoh et al. |
| 6,103,033 | A | 8/2000 | Say et al. |
| 6,120,676 | A | 9/2000 | Heller et al. |
| 6,129,823 | A | 10/2000 | Hughes et al. |
| 6,143,164 | A | 11/2000 | Heller et al. |
| 6,153,069 | A | 11/2000 | Pottgen et al. |
| 6,156,173 | A | 12/2000 | Gotoh et al. |
| 6,193,873 | B1 | 2/2001 | Ohara et al. |
| 6,241,862 | B1 | 6/2001 | McAleer et al. |
| 6,258,229 | B1 | 7/2001 | Winarta et al. |
| 6,270,637 | B1 | 8/2001 | Crismore et al. |
| 6,284,125 | B1 | 9/2001 | Hodges et al. |
| 6,287,451 | B1 | 9/2001 | Winarta et al. |
| 6,299,757 | B1 | 10/2001 | Feldman et al. |
| 6,309,526 | B1 | 10/2001 | Fujiwara et al. |
| 6,338,790 | B1 | 1/2002 | Feldman et al. |
| 6,377,894 | B1 | 4/2002 | Deweese et al. |
| 6,413,213 | B1 | 7/2002 | Essenpreis et al. |
| 6,413,411 | B1 | 7/2002 | Pottgen et al. |
| 6,436,256 | B1 | 8/2002 | Williams et al. |
| 6,448,067 | B1 | 9/2002 | Tajnaföl |
| 6,461,496 | B1 | 10/2002 | Feldman et al. |
| 6,471,839 | B1 | 10/2002 | Yamamoto et al. |
| 6,491,803 | B1 | 12/2002 | Shen et al. |
| 6,503,381 | B1 | 1/2003 | Gotoh et al. |
| 6,531,040 | B2 | 3/2003 | Musho et al. |
| 6,540,891 | B1 | 4/2003 | Stewart et al. |
| 6,565,738 | B1 | 5/2003 | Henning et al. |
| 6,572,745 | B2 | 6/2003 | Rappin et al. |
| 6,591,125 | B1 | 7/2003 | Buse et al. |
| 6,733,655 | B1 | 5/2004 | Davies et al. |
| 6,743,635 | B2 | 6/2004 | Neel et al. |
| 6,773,671 | B1 | 8/2004 | Lewis et al. |
| 6,814,844 | B2 * | 11/2004 | Bhullar et al. ......... 204/403.01 |
| 6,946,299 | B2 | 9/2005 | Neel et al. |
| 6,953,693 | B2 | 10/2005 | Neel et al. |
| 6,959,247 | B2 | 10/2005 | Neel et al. |
| 6,964,871 | B2 | 11/2005 | Bell et al. |
| 7,160,251 | B2 | 1/2007 | Neel et al. |
| 2002/0053523 | A1 | 5/2002 | Liamos et al. |
| 2002/0084196 | A1 | 7/2002 | Liamos et al. |
| 2002/0092612 | A1 | 7/2002 | Davies et al. |
| 2002/0146835 | A1 | 10/2002 | Modzelewski et al. |
| 2002/0148739 | A2 | 10/2002 | Liamos et al. |
| 2002/0157947 | A1 | 10/2002 | Rappin et al. |
| 2002/0157948 | A2 | 10/2002 | Liamos et al. |
| 2002/0160517 | A1 | 10/2002 | Modzelewski et al. |
| 2002/0185385 | A1 | 12/2002 | Charlton |
| 2003/0032875 | A1 | 2/2003 | Tanilike et al. |
| 2003/0036202 | A1 | 2/2003 | Teodorcyzk et al. |
| 2003/0155237 | A1 * | 8/2003 | Surridge et al. ........ 204/403.14 |
| 2003/0203498 | A1 | 10/2003 | Neel et al. |
| 2005/0019953 | A1 | 1/2005 | Groll |
| 2005/0059872 | A1 | 3/2005 | Shartle et al. |
| 2006/0191787 | A1 | 8/2006 | Wang et al. |
| 2007/0110615 | A1 | 5/2007 | Neel et al. |
| 2008/0112852 | A1 | 5/2008 | Neel et al. |

FOREIGN PATENT DOCUMENTS

| | | |
|---|---|---|
| EP | 0 471 986 | 2/1992 |
| EP | 0 735 363 | 10/1996 |
| EP | 1 074 832 | 2/2001 |
| EP | 1 152 239 | 11/2001 |
| JP | 05-340915 | 12/1993 |
| JP | 09-222411 | 8/1997 |
| JP | 11-108879 | 4/1999 |
| JP | 2001-520367 | 10/2001 |
| TW | 356516 | 4/1999 |
| TW | 369599 | 9/1999 |
| WO | WO 99/05516 | 2/1999 |
| WO | WO 99/19507 | 4/1999 |
| WO | WO 01/67099 | 9/2001 |
| WO | WO 01/71328 | 9/2001 |
| WO | WO 01/73109 A2 | 10/2001 |
| WO | WO 01/73124 | 10/2001 |
| WO | WO 03/091717 | 11/2003 |

OTHER PUBLICATIONS

International Search Report, PCT/US2008/081533, dated Feb. 9, 2009.

Taiwanese Office Action dated Dec. 30, 2008, for app. 092109735.

Japanese Office Action in Japanese Patent Application No. 2004-500056 dated Mar. 3, 2009.

Lance S. Kuhn, "Biosensors: Blockbuster or Bomb?, Electrochemical Biosensors for Diabetes Monitoring," *The Electrochemical Society Interface*, pp. 26-31, Winter 1998.

International Search Report in PCT/US2005/002202, Home Diagnostics, Inc. dated Jan. 25, 2005.

International Search Report in PCT/US04/10952, Home Diagnostics, Inc. dated Apr. 14, 2005.

Supplementary European Search Report issued by the European Patent Office on Jun. 12, 2006, in Application No. 03747325.3-2204 PCT/US0312899.

International Preliminary Report on Patentability (Chapter 1 of the PCT) dated Jul. 27, 2006, for International Application No. PCT/US2005/002202.

Japanese Office Action in Japanese Patent Application No. 2004-500056 dated Jun. 29, 2010.

\* cited by examiner

SYSTEMS AND METHODS FOR BLOOD GLUCOSE SENSING

CROSS-REFERENCE TO RELATED APPLICATIONS

This application is a continuation of application Ser. No. 10/706,458, filed Nov. 12, 2003, now abandoned, which is a divisional of U.S. patent application Ser. No. 10/286,648, filed Nov. 1, 2002, now U.S. Pat. No. 6,743,635, issued on Jun. 1, 2004, which claims the benefit of priority to U.S. Provisional Patent Application Nos. 60/375,017, 60/375,019, 60/375,020, 60/375,054, all filed on Apr. 25, 2002, the entire disclosures of which are incorporated herein by reference.

BACKGROUND

1. Field of the Invention

The present invention relates to electrochemical sensors and, more particularly, to systems and methods for sensing blood glucose levels electrochemically.

2. Description of Related Art

Many people, such as diabetics, have a need to monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood sample.

Among the various technologies available for measuring blood glucose levels, electrochemical technologies are particularly desirable because only a very small blood sample may be needed to perform the measurement. In electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current.

It should be emphasized that accurate measurements of blood glucose levels may be critical to the long-term health of many users. As a result, there is a need for a high level of reliability in the meters and test strips used to measure blood glucose levels. However, as sample sizes become smaller, the dimensions of the sample chamber and electrodes in the test strip also become smaller. This, in turn, may make test strips become more sensitive to smaller manufacturing defects and to damage from subsequent handling.

Accordingly, there is a need to provide blood glucose measuring systems and methods with features for measuring blood glucose levels conveniently and reliably.

SUMMARY

In a first principal aspect, the present invention provides a test strip for testing a blood sample. The test strip comprises a sample chamber for the blood sample, at least four electrodes for measuring at least one electrical characteristic of the blood sample in the sample chamber, a plurality of electrical contacts electrically connected to the at least four electrodes, and at least one auto-on electrical contact electrically isolated from the at least four electrodes. The at least four electrodes include a working electrode, a counter electrode, a fill-detect anode, and a fill-detect cathode.

In a second principal aspect, the present invention provides a method of making a plurality of test strips. In accordance with the method, a plurality of test strip structures are formed on one sheet, and the test strip structures are separated into test strips. Each of the test strip structures includes a sample chamber, a plurality of electrodes (including a working electrode, a counter electrode, a fill-detect anode, and a fill-detect cathode), a plurality of electrical contacts electrically connected to the electrodes, and at least one auto-on electrical contact electrically isolated from the plurality of electrodes.

In a third principal aspect, the present invention provides a method of using a test strip to test a blood sample. The test strip includes a sample chamber, a working electrode, a counter electrode, a pair of fill-detect electrodes, and an auto-on conductor. In accordance with the method, the test strip is inserted into a meter that is in a sleep mode. The meter detects an auto-on current through the auto-on conductor and responsively enters an active mode. The blood sample is applied to the sample chamber. The meter detects the blood sample in the sample chamber by applying a fill-detect voltage between the fill-detect electrodes and measuring a fill-detect current flowing between the fill-detect electrodes. The meter applies an assay voltage between the working and counter electrodes and makes at least one measurement of the resulting current. The meter determines a test result from the at least one current measurement.

In a fourth principal aspect, the present invention provides a method of strip identification. A strip that includes an auto-on conductor is inserted into a meter that is in a sleep mode. The meter detects the strip by detecting a current flow through the auto-on conductor, and responsively enters an active mode. The meter measures a voltage drop across the auto-on conductor and identifies the strip as either a test strip or a check strip based on the voltage drop. If the strip is a test strip, the meter performs a test strip sequence. If the strip is a check strip, the meter performs a check strip sequence.

In a fifth principal aspect, the present invention provides a removable data storage device for a meter that uses test strips to measures glucose levels in blood samples. The removable data storage device comprises a carrier, a circuit board mounted to the carrier, and a memory mounted to the circuit board. The carrier has a proximal end and a distal end and is keyed for inserting the distal end into the-meter in a preferred orientation. The circuit board includes a plurality of electrical contacts for electrically connecting to the meter. The plurality of electrical contacts includes a ground contact and a voltage supply contact. The ground contact extends closer to the distal end than the voltage supply contact. The memory stores data for use by the meter, including calibration coefficients for a plurality of test strips. The memory is electrically connected to the plurality of electrical contacts on the circuit board. When the removable data storage device is inserted into the meter in the preferred orientation, the ground contact becomes electrically connected to the meter before the voltage supply contact.

In a sixth principal aspect, the present invention provides a meter for use in combination with a test strip. The test strip includes a working electrode, a counter electrode, a pair of fill-detect electrodes, and an auto-on conductor. The meter comprises a strip connector for receiving the test strip, a processor, a memory, a plurality of machine instructions stored in the memory and executable by the processor for performing a test strip sequence, and a data acquisition system controlled by the processor. When the test strip is inserted in the strip connector, the data acquisition system applies at least a first voltage between the working and counter electrodes and measures any resulting current flowing between the working and counter electrodes, applies at least a second voltage between the fill-detect electrodes and measures any resulting current flowing between the fill-detect electrodes, and measures a voltage drop across the auto-on conductor. The data acquisition system includes at least one digital-to-analog converter and at least one analog-to-digital converter.

DETAILED DESCRIPTION OF THE PREFERRED EMBODIMENTS

Figure 1:
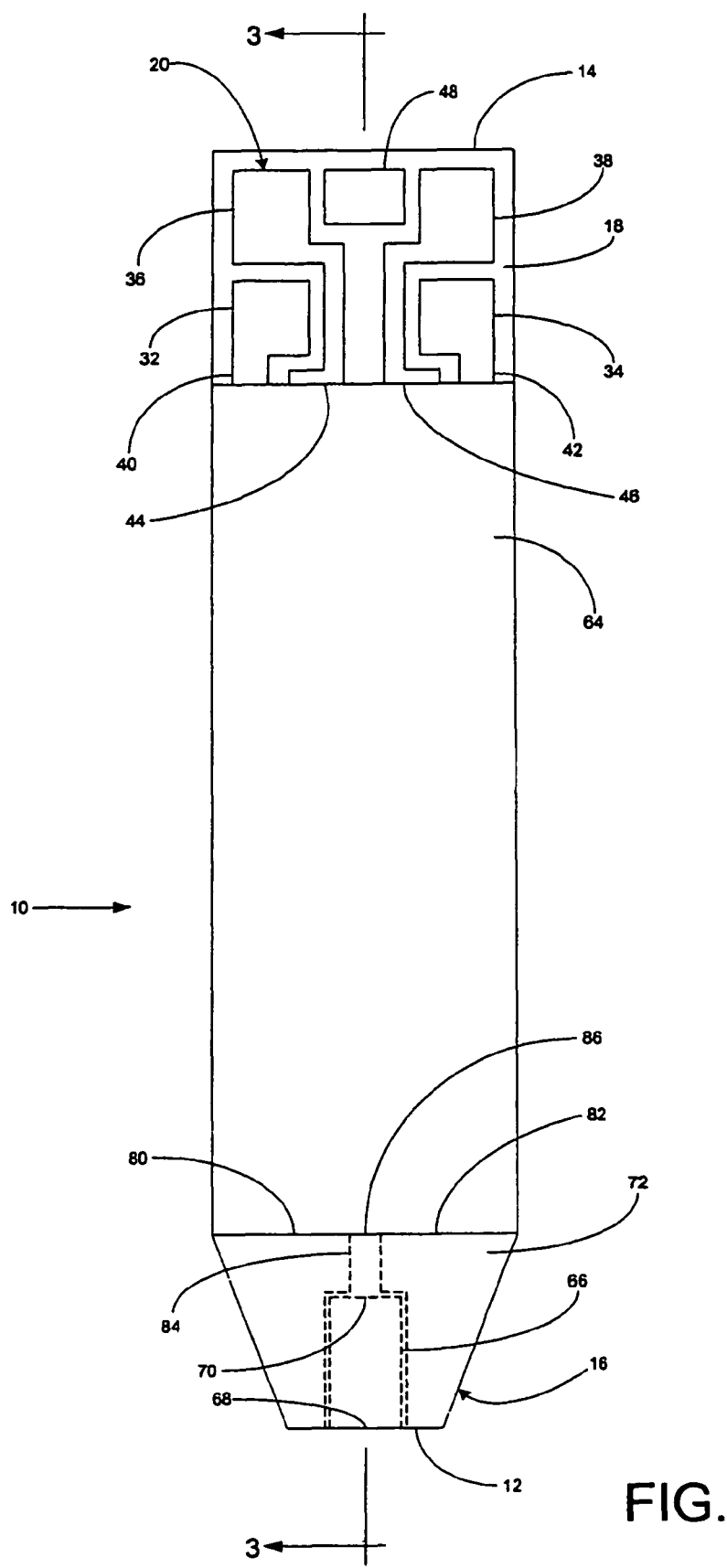
FIG. 1 is a top plan view of a test strip, in accordance with a preferred embodiment of the present invention.

In accordance with a preferred embodiment, a system for measuring a glucose level in a blood sample includes a test strip and a meter. The system may also include a removable data storage device associated with a lot of test strips. The removable data storage device stores data for use by the meter, such as calibration coefficients for test strips from that lot. The system may also include a check strip that the user may insert into the meter to check that the meter is functioning properly.

The test strip includes a sample chamber for receiving the blood sample. The sample chamber has a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip may include a tapered section that is narrowest at the proximal end, in order to make it easier for the user to locate the first opening and apply the blood sample.

A working electrode, a counter electrode, a fill-detect electrode, and a fill-detect anode are disposed in the sample chamber. A reagent layer is disposed in the sample chamber and preferably covers at least the working electrode. The reagent layer may include an enzyme, such as glucose oxidase, and a mediator, such as potassium ferricyanide. The test strip has, near its distal end, a plurality of electrical contacts that are electrically connected to the electrodes via conductive traces. The test strip also has near its distal end an auto-on conductor, which may be electrically isolated from the electrodes.

The meter may be battery powered and may stay in a low-power sleep mode when not in use in order to save power. When the test strip is inserted into the meter, the electrical contacts on the test strip contact corresponding electrical contacts in the meter. In addition, the auto-on conductor bridges a pair of electrical contacts in the meter, causing a current to flow through the auto-on conductor. The current flow through the auto-on conductor causes the meter to wake up and enter an active mode. The meter also measures the voltage drop across the auto-on conductor and identifies the inserted strip as either a test strip or a check strip based on the voltage drop. If the meter detects a check strip, it performs a check strip sequence. If the meter detects a test strip, it performs a test strip sequence.

In the test strip sequence, the meter validates the working electrode, counter electrode, and fill-detect electrodes by confirming that there are no low-impedance paths between any of these electrodes. If the electrodes are valid, the meter indicates to the user that sample may be applied to the test strip. The meter then applies a drop-detect voltage between the working and counter electrodes and detects the blood sample by detecting a current flow between the working and counter electrodes (i.e., a current flow through the blood sample as it bridges the working and counter electrodes). To detect that adequate sample is present in the sample chamber and that the blood sample has traversed the reagent layer and mixed with the chemical constituents in the reagent layer, the meter applies a fill-detect voltage between the fill-detect electrodes and measures any resulting current flowing between the fill-detect electrodes. If this resulting current reaches a sufficient level within a predetermined period of time, the meter indicates to the user that adequate sample is present and has mixed with the reagent layer.

The meter waits for an incubation period of time after initially detecting the blood sample, to allow the blood sample to react with the reagent layer. Then, during a measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the glucose level in the blood sample. The meter calculates the glucose level based on the measured current and on calibration data that the meter previously downloaded from the removable data storage device associated with the test strip and stored in the meter's memory. The meter then displays the calculated glucose level to the user.

1. Test Strip Configuration

Figure 2:
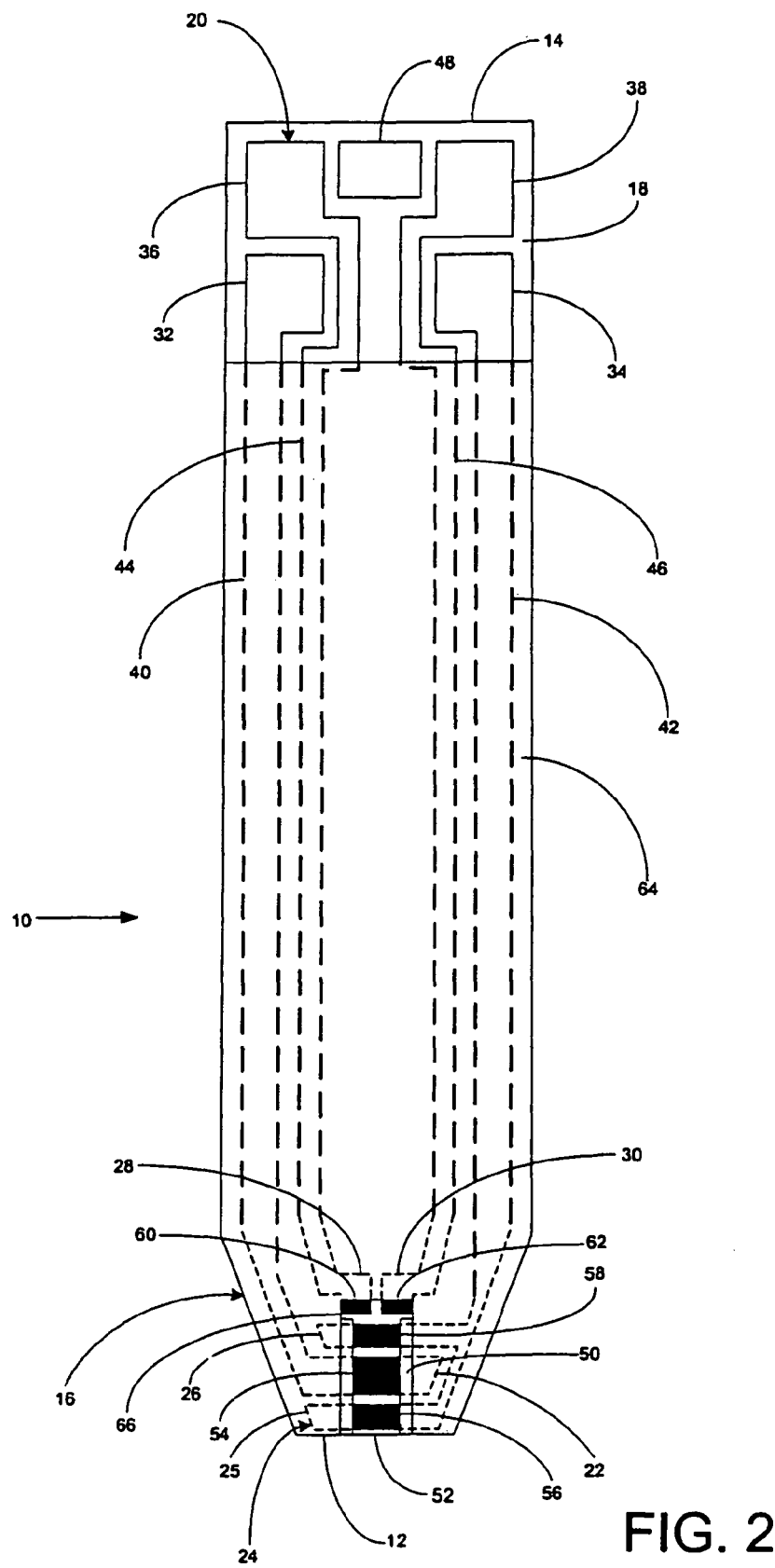
FIG. 2 is a top plan view of the test strip of FIG. 1, with the cover, adhesive layer, and reagent layer cut away, in accordance with a preferred embodiment of the present invention.
Figure 3:
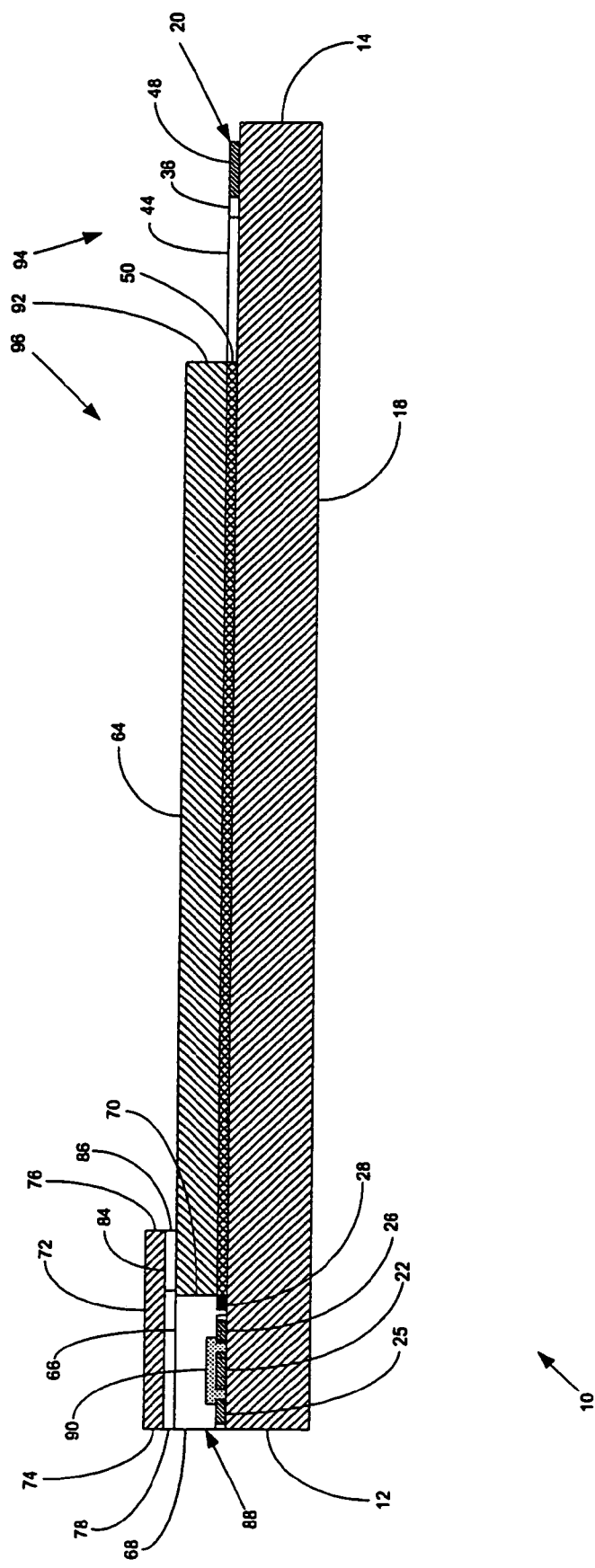
FIG. 3 is a cross-sectional view of the test strip of FIG. 1, taken along line 3-3, in accordance with a preferred embodiment of the present invention.

With reference to the drawings, FIGS. 1, 2, and 3 show a test strip 10, in accordance with a preferred embodiment of the present invention. Test strip 10 preferably takes the form of a generally flat strip that extends from a proximal end 12 to a distal end 14. Preferably, test strip 10 is sized for easy handling. For example, test strip 10 may be about 1⅜ inches along its length (i.e., from proximal end 12 to distal end 14) and about 5/16 inches wide. However, proximal end 12 may be narrower than distal end 14. Thus, test strip 10 may include a tapered section 16, in which the full width of test strip 10 tapers down to proximal end 12, making proximal end 12 narrower than distal end 14. As described in more detail below, the user applies the blood sample to an opening in proximal end 12 of test strip 10. Thus, providing tapered section 16 in test strip 10, and making proximal end 12 narrower than distal end 14, may help the user to locate the opening where the blood sample is to be applied and may make it easier for the user to successfully apply the blood sample to test strip 10.

As best shown in FIG. 3, test strip 10 may have a generally layered construction. Working upward from the lowest layer, test strip 10 may include a base layer 18 extending along the entire length of test strip 10. Base layer 18 is preferably composed of an electrically insulating material and has a thickness sufficient to provide structural support to test strip 10. For example, base layer 18 maybe polyester that is about 0.014 inches think.

Disposed oh base layer 18 is a conductive pattern 20. Conductive pattern 20 includes a plurality of electrodes disposed on base layer 18 near proximal end 12, a plurality of electrical contacts disposed on base layer 18 near distal end 14, and a plurality of conductive traces electrically connecting the electrodes to the electrical contacts. In a preferred embodiment, the plurality of electrodes includes a working electrode 22, a counter electrode 24, which may include a first section 25 and a second section 26, a fill-detect anode 28, and a fill-detect cathode 30. Correspondingly, the electrical contacts may include a working electrode contact 32, a counter electrode contact 34, a fill-detect anode contact 36, and a fill-detect cathode contact 38. The conductive traces may include a working electrode trace 40, electrically connecting working electrode 22 to working electrode contact 32, a counter electrode trace 42, electrically connecting counter electrode 24 to counter electrode contact 34, a fill-detect anode trace 44 electrically connecting fill-detect anode 28 to fill-detect contact 36, and a fill-detect cathode trace 46 electrically connecting fill-detect cathode 30 to fill-detect cathode contact 38. In a preferred embodiment, conductive pattern 20 also includes an auto-on conductor 48 disposed on base layer 18 near distal end 14.

A dielectric layer 50 may also be disposed on base layer 18, so as to cover portions of conductive pattern 20. Preferably, dielectric layer 50 is a thin layer (e.g., about 0.0005 inches thick) and is composed of an electrically insulating material, such as silicones, acrylics, or mixtures thereof. Dielectric layer 50 may cover portions of working electrode 22, counter electrode 24, fill-detect anode 28, fill-detect cathode 30, and conductive traces 40-46, but preferably does not cover electrical contacts 32-38 or auto-on conductor 48. For example, dielectric layer 50 may cover substantially all of base layer 18, and the portions of conductive pattern 20 thereon, from a line just proximal of contacts 32 and 34 all the way to proximal end 12, except for a slot 52 extending from proximal end 12. In this way, slot 52 may define an exposed portion 54 of working electrode 22, exposed portions 56 and 58 of sections 25 and 26 of counter electrode 24, an exposed portion 60 of fill-detect anode 28, and an exposed portion 62 of fill-detect cathode 30. As shown in FIG. 2, slot 52 may have different widths in different sections, which may make exposed portions 60 and 62 of fill-detect electrodes 28 and 30 wider than exposed portions 54, 56, and 58 of working electrode 22 and counter electrode sections 25 and 26.

The next layer in test strip 10 may be a dielectric spacer layer 64 disposed on dielectric layer 50. Dielectric spacer layer 64 is composed of an electrically insulating material, such as polyester. Dielectric spacer layer 64 may have a length and width similar to that of dielectric layer 50. In addition, spacer 64 may include a slot 66 that is substantially aligned with slot 52. Thus, slot 66 may extend from a proximal end 68, aligned with proximal end 12, back to a distal end 70, such that exposed portions 54-62 of working electrode 22, counter electrode 24, fill-detect anode 28, and fill-detect cathode 30 are located in slot 66.

A cover 72, having a proximal end 74 and a distal end 76, may be attached to dielectric spacer layer 64 via an adhesive layer 78. Cover 72 is composed of an electrically insulating material, such as polyester, and may have a thickness of about 0.004 inches. Preferably, cover 72 is transparent.

Adhesive layer 78 may include a polyacrylic or other adhesive and have a thickness of about 0.0005 inches. Adhesive layer 78 may consist of a first section 80 and a second section 82 disposed on spacer 64 on opposite sides of slot 66. A break 84 in adhesive layer 78 between sections 80 and 82 extends from distal end 70 of slot 66 to an opening 86. Cover 72 may be disposed on adhesive layer 78 such that its proximal end 74 is aligned with proximal end 12 and its distal end 76 is aligned with opening 86. In this way, cover 72 covers slot 66 and break 84.

Slot 66, together with base layer 18 and cover 72, defines a sample chamber 88 in test strip 10 for receiving a blood sample for measurement. Proximal end 68 of slot 66 defines a first opening in sample chamber 88, through which the blood sample is introduced into sample chamber 88. At distal end 70 of slot 66, break 84 defines a second opening in sample chamber 88, for venting sample chamber 88 as sample enters sample chamber 88. Slot 66 is dimensioned such that a blood sample applied to its proximal end 68 is drawn into and held in sample chamber 88 by capillary action, with break 84 venting sample chamber 88 through opening 86, as the blood sample enters. Moreover, slot 66 is dimensioned so that the blood sample that enters sample chamber 88 by capillary action is about 1 microliter or less. For example, slot 66 may have a length (i.e., from proximal end 68 to distal end 70) of about 0.140 inches, a width of about 0.060 inches, and a height (which may be substantially defined by the thickness of dielectric spacer layer 64) of about 0.005 inches. Other dimensions could be used, however.

A reagent layer 90 is disposed in sample chamber 88. Preferably, reagent layer 90 covers at least exposed portion 54 of working electrode 22. Most preferably, reagent layer 90 also at least touches exposed portions 56 and 58 of counter electrode 24. Reagent layer 90 includes chemical constituents to enable the level of glucose in the blood sample to be determined electrochemically. Thus, reagent layer 90 may include an enzyme specific for glucose, such as glucose oxidase, and a mediator, such as potassium ferricyanide. Reagent layer 90 may also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

With these chemical constituents, reagent layer 90 reacts with glucose in the blood sample in the following way. The glucose oxidase initiates a reaction that oxidizes the glucose to gluconic acid and reduces the ferricyanide to ferricyanide. When an appropriate voltage is applied to working electrode 22, relative to counter electrode 24, the ferricyanide is oxidized to ferricyanide, thereby generating a current that is related to the glucose concentration in the blood sample.

As best shown in FIG. 3, the arrangement of the various layers in test strip 10 may result in test strip 10 having different thicknesses in different sections. In particular, among the layers above base layer 18, much of the thickness of test strip 10 may come from the thickness of spacer 64. Thus, the edge of spacer 64 that is closest to distal end 14 may define a shoulder 92 in test strip 10. Shoulder 92 may define a thin section 94 of test strip 10, extending between shoulder 92 and distal end 14, and a thick section 96, extending between shoulder 92 and proximal end 12. The elements of test strip 10 used to electrically connect it to the meter, namely, electrical contacts 32-38 and auto-on conductor 48, may all be located in thin section 94. Accordingly, the connector in the meter may be sized so as to be able to receive thin section 94 but not thick section 96, as described in more detail below. This may beneficially cue the user to insert the correct end, i.e., distal end 14, in thin section 94, and may prevent the user from inserting the wrong end, i.e., proximal end 12 in thick section 96, into the meter.

Although FIGS. 1-3 illustrate a preferred configuration of test strip 10, other configurations could be used. For example, in the configuration shown in FIGS. 1-3, counter electrode 24 is made up two sections, a first section 25 that is on the proximal side of working electrode 22 and a second section 26 that is on the distal side of working electrode 22. Moreover, the combined area of the exposed portions 56 and 58 of counter electrode 24 is preferably greater than the area of the exposed portion 54 of working electrode 22. In this configuration, counter electrode 24 effectively surrounds working electrode 22, which beneficially shields working electrode 22 electrically. In other configurations, however, counter electrode 24 may have only one section, such as first section 25.

Different arrangements of fill-detect electrodes 28 and 30 may also be used. In the configuration shown in FIGS. 1-3, fill-detect electrodes 28 and 30 are in a side-by-side arrangement. Alternatively, fill-detect electrodes 28 and 30 may be in a sequential arrangement, whereby, as the sample flows through sample chamber 88 toward distal end 70, the sample contacts one of the fill-detect electrodes first (either the anode or the cathode) and then contacts the other fill-detect electrode. In addition, although exposed portions 60 and 62 of fill-detect electrodes 28 and 30 are wider than exposed portions 54, 56, and 58 of working electrode 22 and counter electrode sections 25 and 26 in the embodiment shown in FIG. 2, they may have the same or a narrower width in other embodiments.

However they are arranged relative to each other, it is preferable for fill-detect electrodes 28 and 30 to be located on the distal side of reagent layer 90. In this way, as the sample flows through sample chamber 88 toward distal end 70, the sample will have traversed reagent layer 90 by the time it reaches fill-detect electrodes 28 and 30. This arrangement beneficially allows the fill-detect electrodes 28 and 30 to detect not only whether sufficient blood sample is present in sample chamber 88 but also to detect whether the blood sample has become sufficiently mixed with the chemical constituents of reagent layer 90. Thus, if reagent layer 90 covers working electrode 22, as is preferable, then it is preferable to locate fill-detect electrodes 28 and 30 on the distal side of working electrode 22, as in the configuration shown in FIG. 1-3. Other configurations may be used, however.

2. Method of Manufacturing Test Strips

Figure 4:
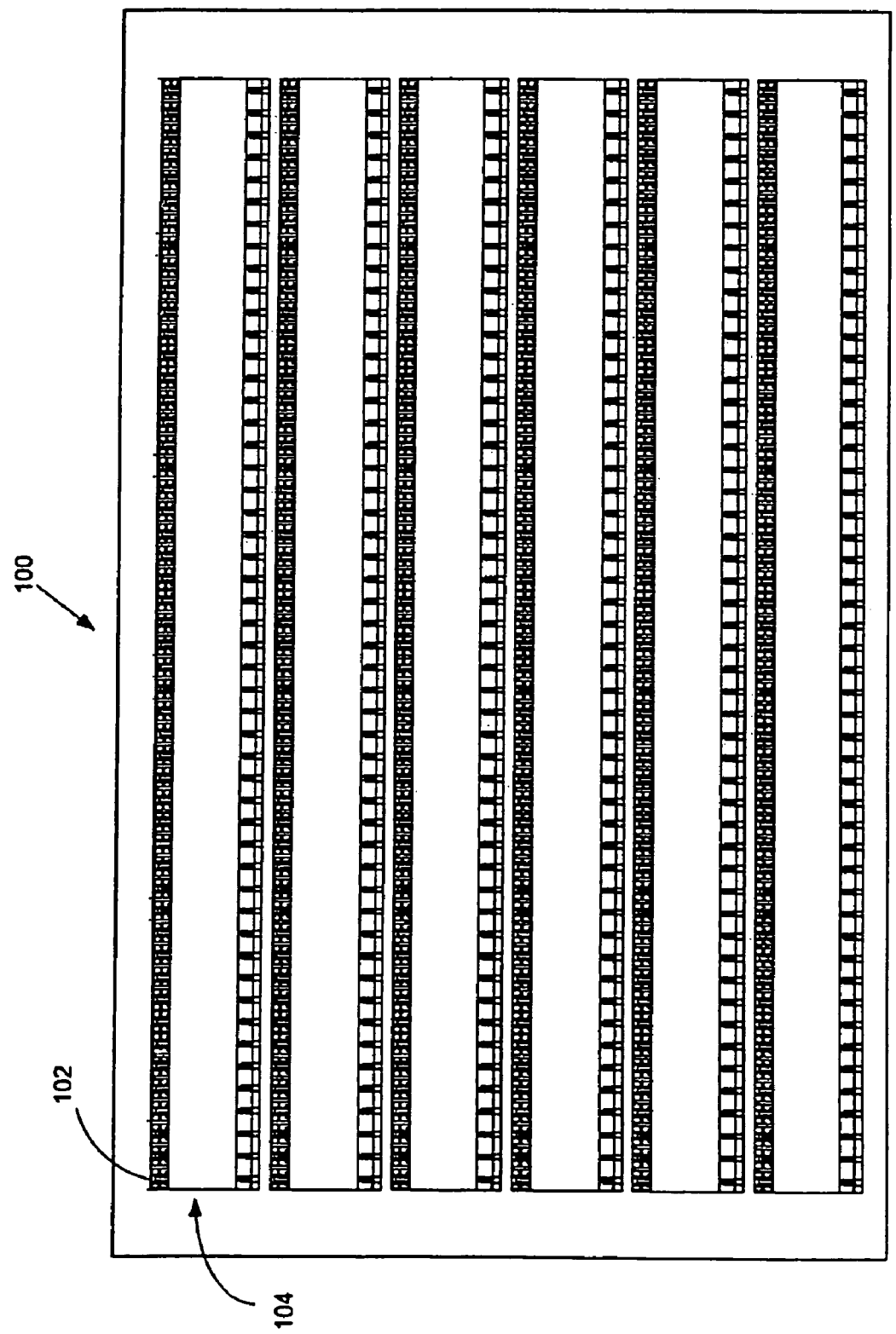
FIG. 4 is a top schematic view of an array of test strip structures, which may be separated into a plurality of test strips of the type shown in FIGS. 1-3, in accordance with a preferred embodiment of the present invention.

With reference to FIG. 4, a plurality of test strips 10 may be mass-produced by forming an integrated structure 100 that includes a plurality of test strip structures 102 all on one sheet. The test strip structures 102 may be arranged in an array that includes a plurality of rows 104 (e.g., six rows), with each row 104 including a plurality of test strip structures 102 (e.g., fifty test strip structures in each row). The plurality of test strips 10 may then be formed by separating the test strip structures 102 from each other. In a preferred separation process, each row 104 of test strip structures 102 is first punched out of integrated structure 100. This punching process may provide some of the outer shape of the test strips 10. For example, the tapered shape of tapered sections 16 of the test strips 10 may be formed in this punching process. Next, a slitting process may be used to separate the test strip structures 102 in each row 104 into individual test strips 10.

FIGS. 5 through 9 show only one test strip structure (either partially or completely fabricated), in order to illustrate various steps in a preferred method for forming the test strip structures 102. In this preferred approach, the test strip structures 102 in integrated structure 100 are all formed on a sheet of material that serves as base layer 18 in the finished test strips 10. The other components in the finished test strips 10 are then built up layer-by-layer on top of base layer 18 to form the test strip structures 102. In each of FIGS. 5 through 9, the outer shape of the test strip 10 that would be formed in the overall manufacturing process is shown as a dotted line.

Figure 5:
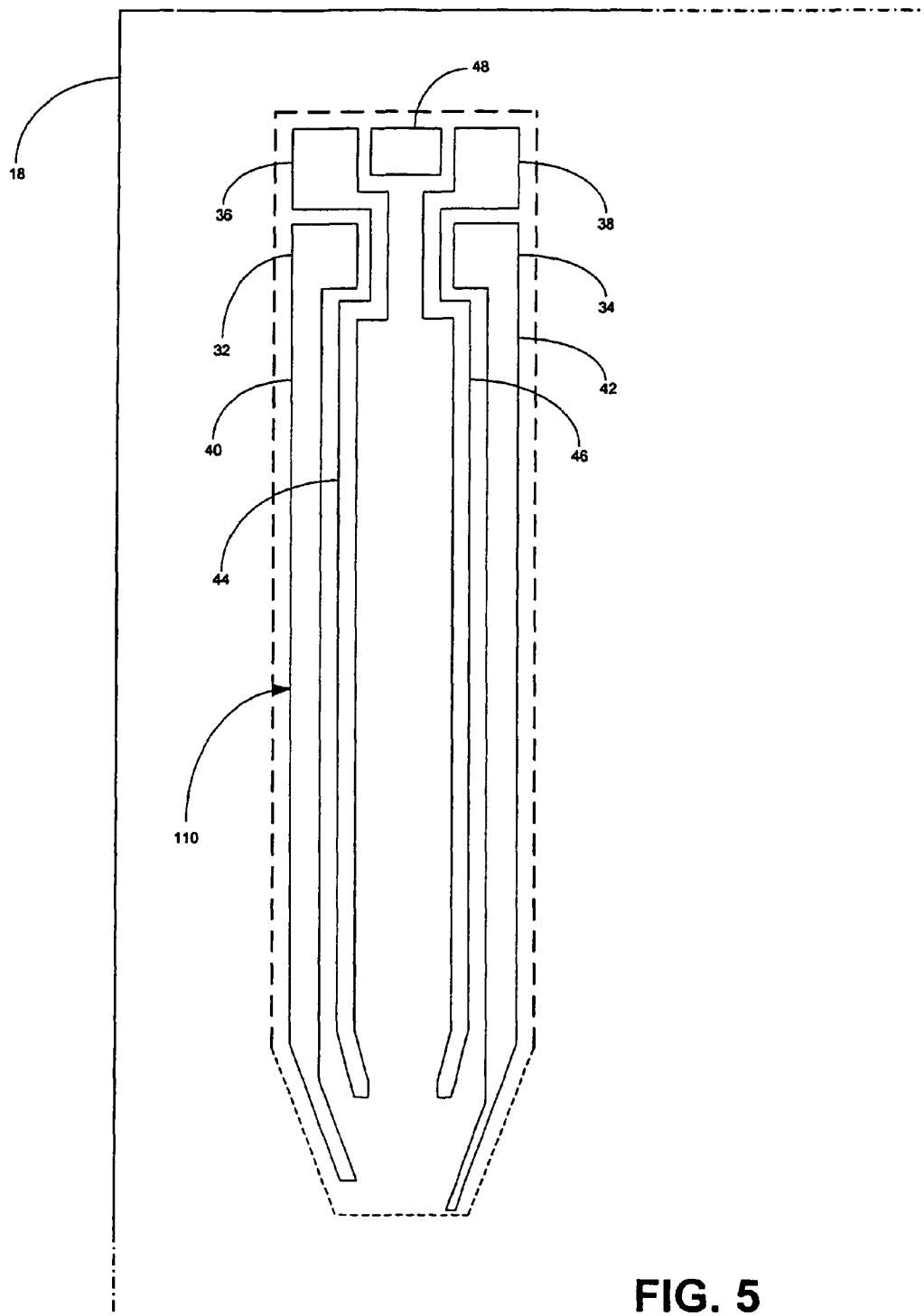
FIG. 5 is top plan view of an intermediate stage in the formation of one of the test strip structures of FIG. 4, in accordance with a preferred embodiment of the present invention.

As shown in FIG. 5; the manufacturing process may begin by forming, for each test strip structure, a first conductive pattern 110 on base layer 18. First conductive pattern 110 may include electrical contacts 32-38, conductive traces 40-42, and auto-on conductor 48. First conductive pattern 110 may be formed by screen-printing a first conductive ink onto base layer 18. The first conductive ink may be provided as a viscous liquid that includes particles of a conductive material, such as metallic silver. For example, a preferred first conductive ink has a composition of about 30-60 weight % metallic silver, about 5-10 weight % lamp black, about 30-60 weight % dipropylene glycol monomethyl ether, and other components, and is available from E.I. DuPont de Nemours & Co., Wilmington, Del., as "Membrane Switch Composition 5524."

Figure 6:
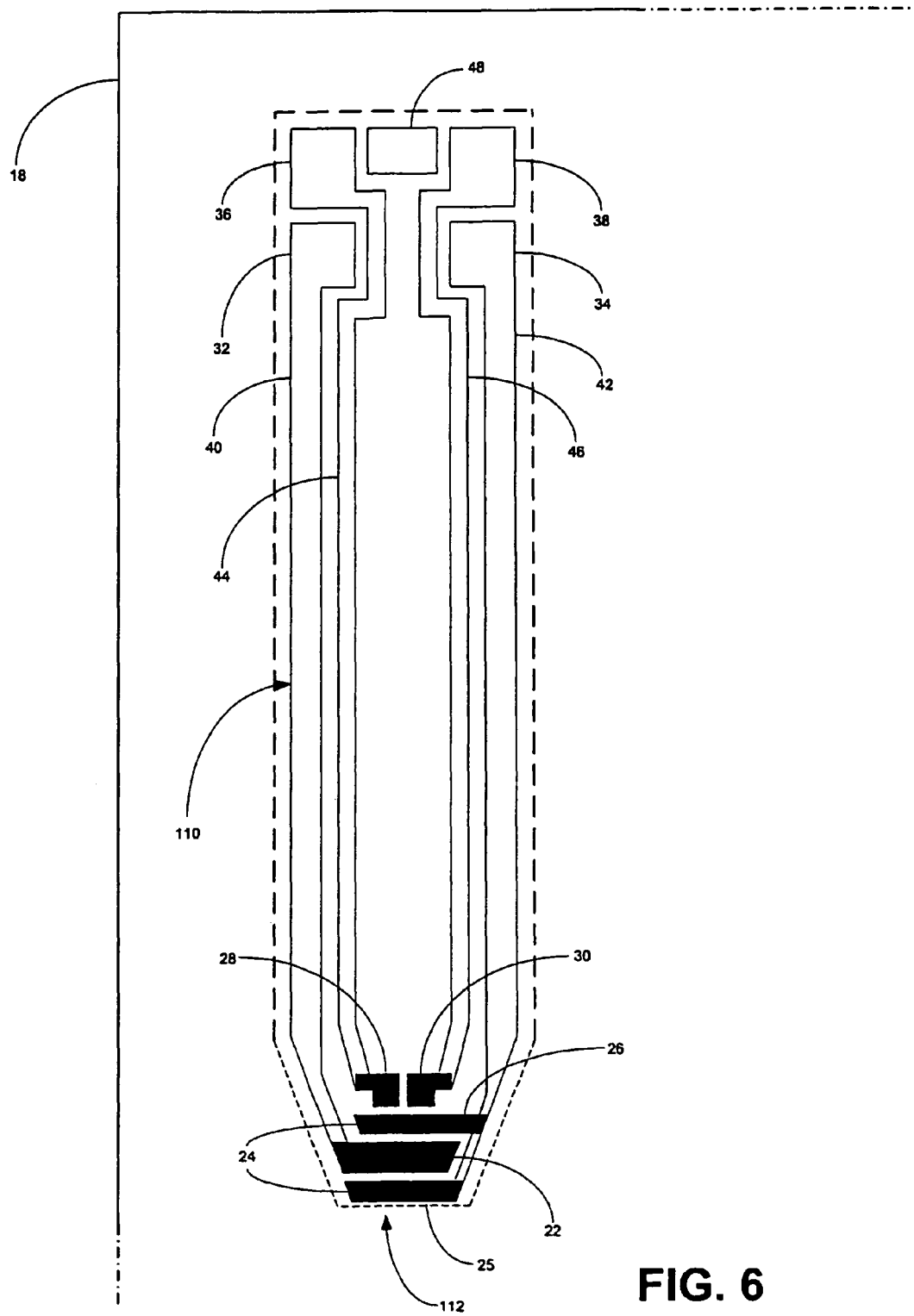
FIG. 6 is top plan view of an intermediate stage in the formation of one of the test strip structures of FIG. 4, in accordance with a preferred embodiment of the present invention.

As shown in FIG. 6, a second conductive pattern 112 may then be formed on base layer 18. Second conductive pattern 112 may include working electrode 22, first section 25 and second section 26 of counter electrode 24, fill-detect anode 28, and fill-detect cathode 30. Second conductive pattern 112 may be formed by screen-printing a second conductive ink onto base layer 18. The second conductive ink may be provided as a viscous liquid that includes particles of a conductive material, such as graphite. The second conductive ink may have a different composition than the first conductive ink. In particular, the second conductive ink is preferably substantially of free of materials, such as silver, that can interfere with the chemistry of reagent layer 90. A preferred second conductive ink has a composition of about 10-20 weight % graphite, about 5-10 weight % lamp black, greater than 60 weight % ethylene glycol diacetate, and about 5-10 weight % polymer, and is available from E.I. DuPont de Nemours & Co., Wilmington, Del., as "E00735-111."

Figure 7:
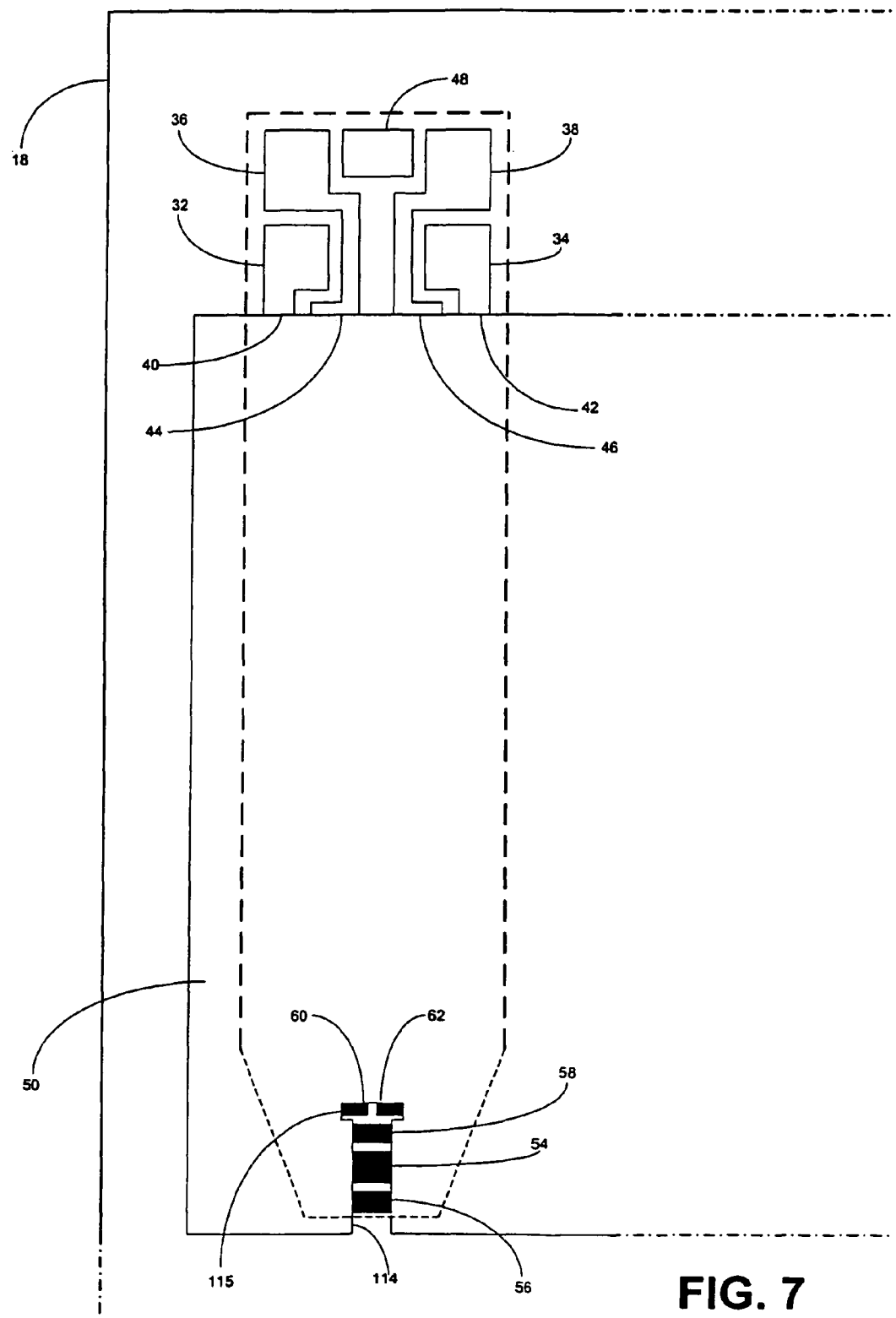
FIG. 7 is top plan view of an intermediate stage in the formation of one of the test strip structures of FIG. 4, in accordance with a preferred embodiment of the present invention.

As shown in FIG. 7, dielectric layer 50 may then be formed on base layer 18 so as to cover portions of first conductive pattern 110 and second conductive pattern 112. As shown in FIG. 7, dielectric layer 50 may extend beyond the outline of a finished test strip 10 so as to cover multiple test strip structures being formed on base layer 18. Also as shown in FIG. 7, dielectric layer 50 may include a slot 114 that defines exposed portions 54, 56, 58, 60, and 62 of working electrode 22, first counter electrode section 25, second counter electrode section 26, fill-detect anode portion 28, and fill-detect cathode portion 30. Slot 52 in test strip 10 corresponds to the part of slot 114 that remains in test strip 10 after the test strip structures are separated into test strips. In this regard, slot 114 may include a wide section 115 to allow the portions of fill-detect electrodes 28 and 30 left exposed by layer 50 to be wider than the portions of working electrode 22 and counter electrode 24 left exposed by layer 50.

In a preferred approach, dielectric layer 50 is applied by screen-printing a dielectric material. A preferred dielectric material comprises a mixture of silicone and acrylic compounds, such as the "Membrane Switch Composition 5018" available from E.I. DuPont de Nemours & Co., Wilmington, Del.

Figure 8:
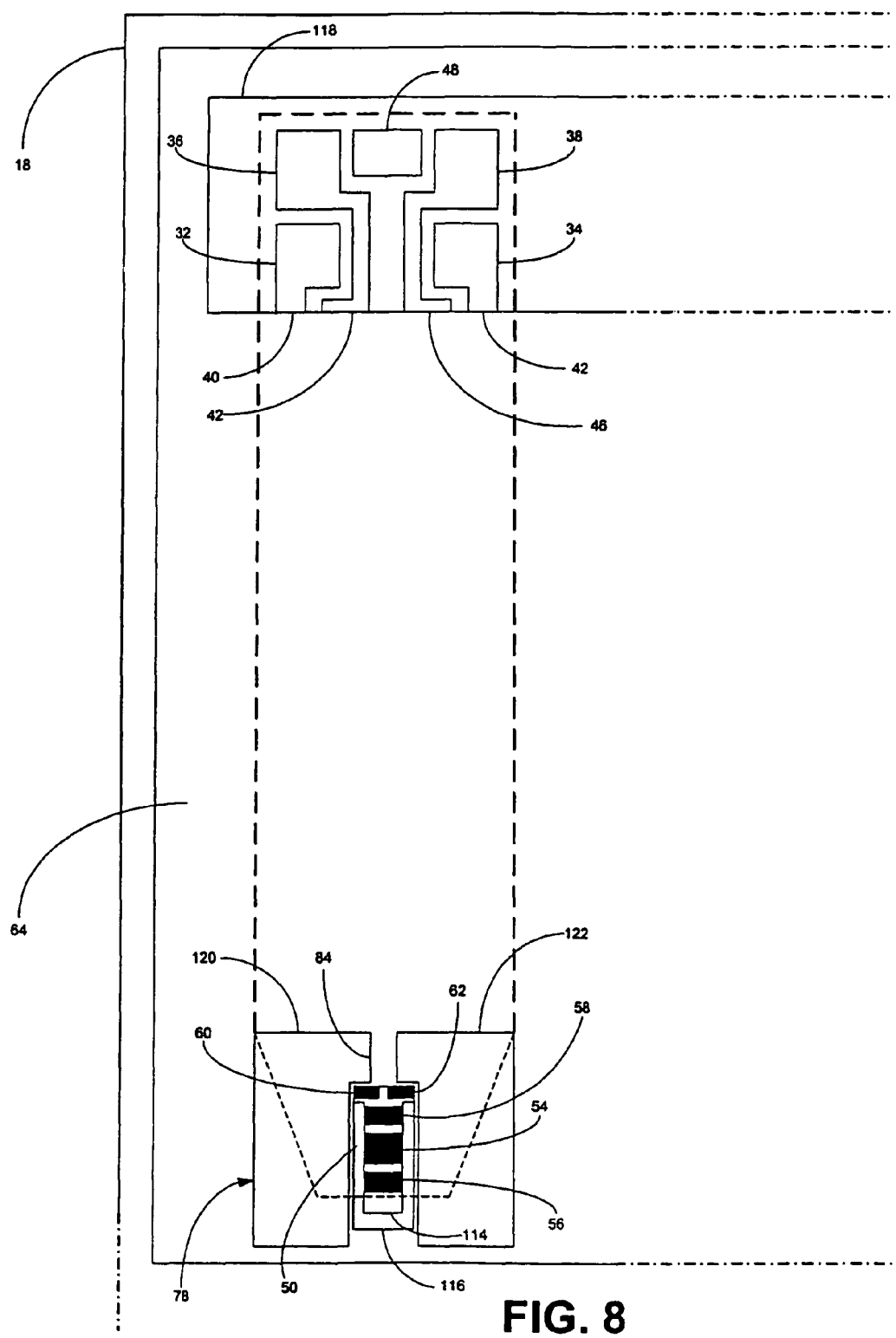
FIG. 8 is top plan view of an intermediate stage in the formation of one of the test strip structures of FIG. 4, in accordance with a preferred embodiment of the present invention.

In the next step, dielectric spacer layer 64 may be applied to dielectric layer 50, as illustrated in FIG. 8. Spacer 64 may be applied to dielectric layer 50 in a number of different ways. In a preferred approach, spacer 64 is provided as a sheet large enough and appropriately shaped to cover multiple test strip structures. In this approach, the underside of spacer 64 may be coated with an adhesive to facilitate attachment to dielectric layer 50 and base layer 18. Portions of the upper surface of spacer 64 may also be coated with an adhesive in order to provide adhesive layer 78 in each of the test strips 10. Various slots may be cut into or punched out of spacer 64 to shape it before spacer layer 64 is applied to dielectric layer 50. For example, as shown in FIG. 8, spacer 64 may have a slot 116 for each test strip structure and a slot 118 that extends over multiple test strip structures. In addition, spacer 64 may include adhesive sections 120 and 122, with break 84 therebetween, for each test strip structure being formed.

Spacer 64 is then positioned over base layer 18, as shown in FIG. 8, and laminated to base layer 18 and dielectric layer 50. When spacer 64 is appropriately positioned on base layer 18, exposed electrode portions 54-62 are accessible through slot 116. Thus, slot 66 in test strip 10 corresponds to that part of slot 116 that remains in test strip 10 after the test strip structures are separated into test strips. Similarly, slot 118 in spacer 64 leaves contacts 32-38 and auto-on conductor 48 exposed after lamination.

Alternatively, spacer 64 could be applied in other ways. For example, spacer 64 may be injection molded onto base layer 18 and dielectric 50. Spacer 64 could also be built up on dielectric layer 50 by screen-printing a dielectric material to the appropriate thickness.

Reagent layer 90 may then be applied to each test strip structure. In a preferred approach, reagent layer 90 is applied by micropipetting an aqueous composition onto exposed portion 54 of working electrode 22 and letting it dry to form reagent layer 90. A preferred aqueous composition has a pH of about 6 and contains 2 weight % polyvinyl alcohol, 0.1 M potassium phosphate, 0.05 weight % Triton X-100, 0.15 M potassium ferricyanide, 0.7% hydroxyethylcellulose (such as NATROSOL®), and about 2500 units of glucose oxidase per mL. Alternatively, other methods, such as screen-printing, may be used to apply the composition used to form reagent layer 90.

Figure 9:
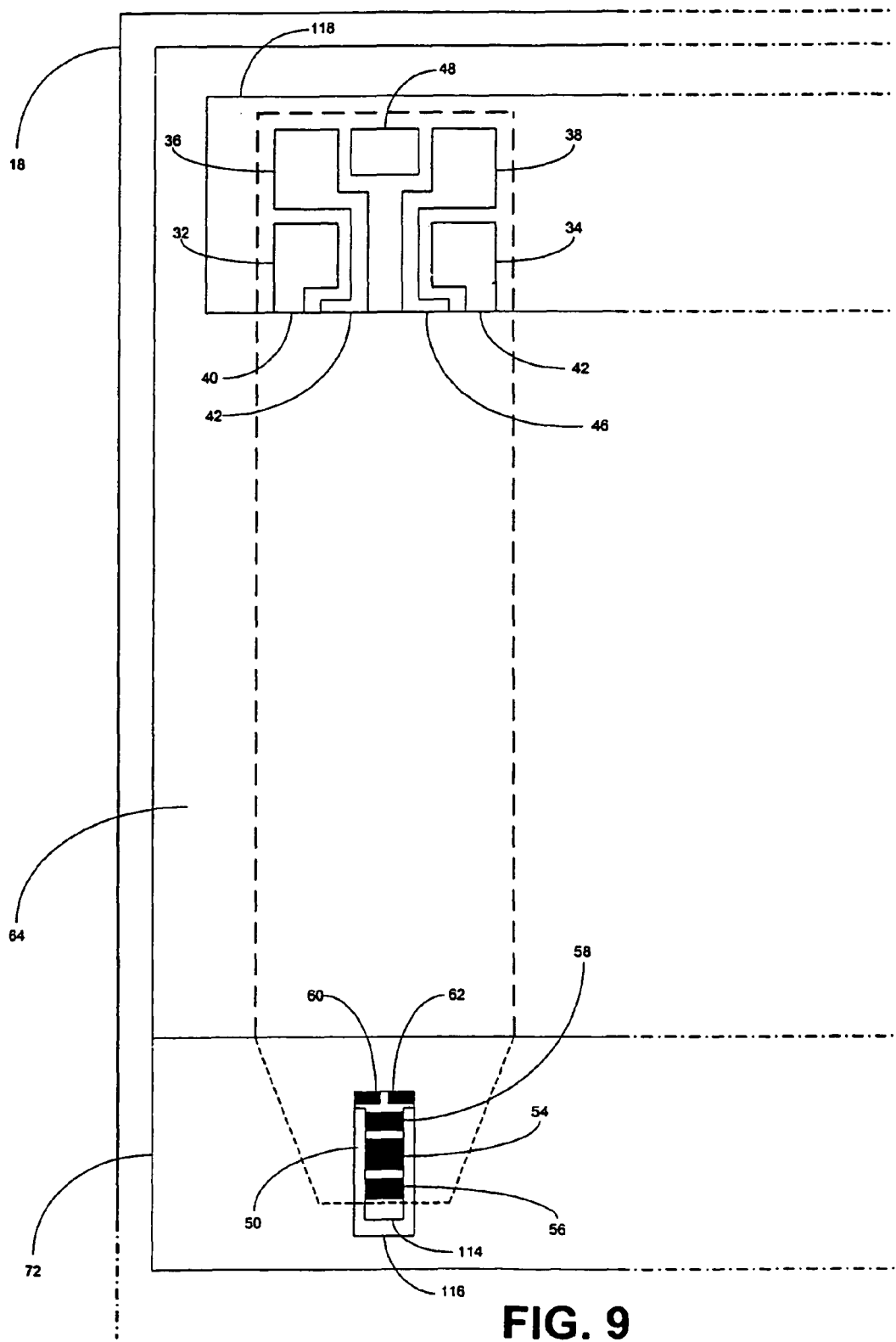
FIG. 9 is top plan view of one of the test strip structures of FIG. 4, in accordance with a preferred embodiment of the present invention.

A transparent cover 72 may then be attached to adhesive layer 78. As shown in FIG. 9, cover 72 (which is shown as transparent) may be large enough to cover multiple test strip structures 102. Attaching cover 72 may complete the formation of the plurality of test strip structures 102. The plurality of test strip structures 102 may then be separated from each other to form a plurality of test strips 10, as described above.

3. The Meter and Removable Data Storage Device

Figure 10:
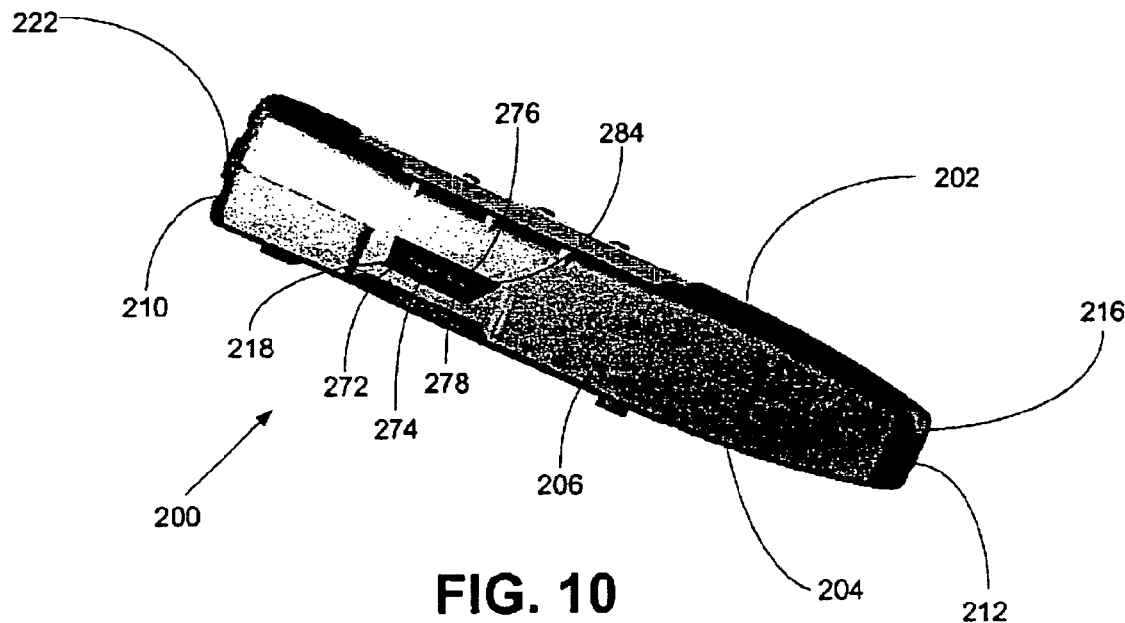
FIG. 10 is a perspective view of a meter, in accordance with a preferred embodiment of the present invention.
Figure 11:
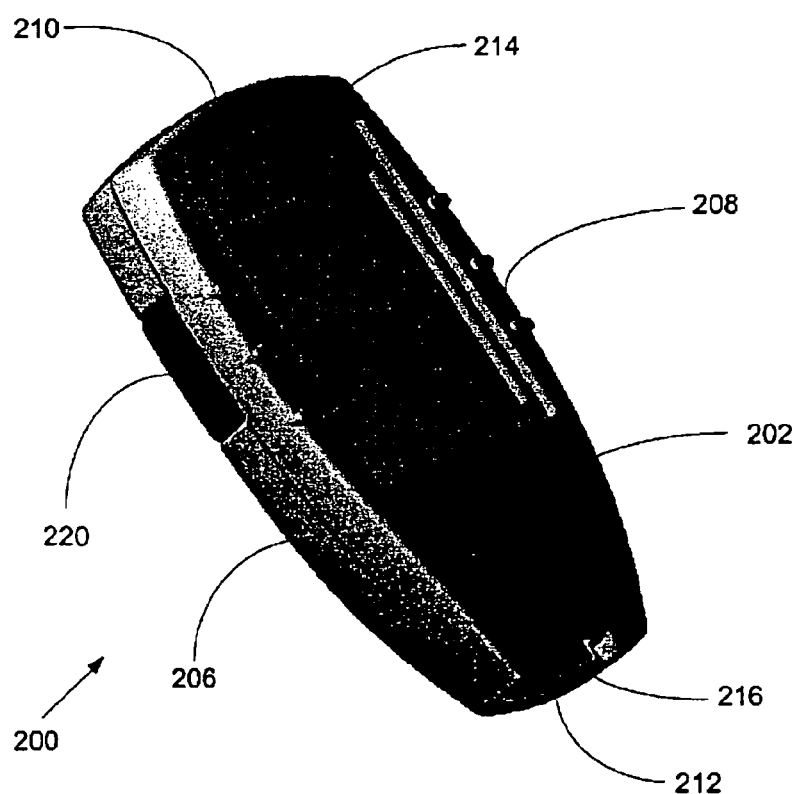
FIG. 11 is a perspective view of the meter of FIG. 10, with a removable data storage device inserted in it, in accordance with a preferred embodiment of the present invention.

To measure the glucose level in a blood sample, test strip 10 is preferably used with a meter 200, as shown in FIGS. 10 and 11. Preferably, meter 200 has a size and shape to allow it to be conveniently held in a user's hand while the user is performing the glucose measurement. Meter 200 may include a front side 202, a back side 204, a left side 206, a right side 208, a top side 210, and a bottom side 212. Front side 202 may include a display 214, such as a liquid crystal display (LCD). Bottom side 212 may include a strip connector 216 into which test strip 10 is inserted to conduct a measurement Left side 206 of meter 200 may include a data connector 218 into which a removable data storage device 220 may be inserted, as described in more detail below. Top side 210 may include one or more user controls 222, such as buttons, with which the user may control meter 200. Right side 208 may include a serial connector (not shown).

Figure 12:
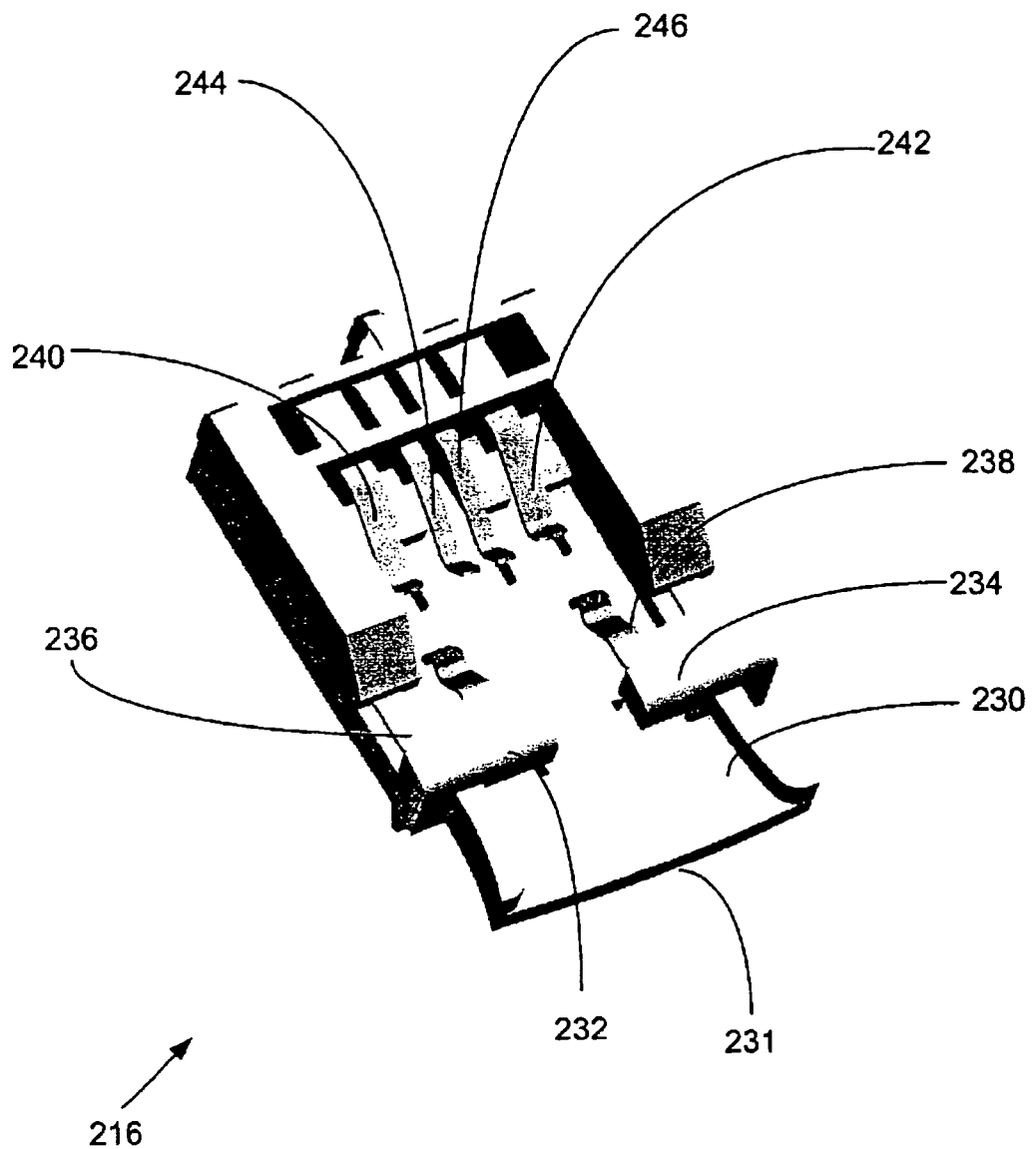
FIG. 12 is a perspective view of a strip connector in the meter of FIG. 10, in accordance with a preferred embodiment of the present invention.

FIG. 12 shows a preferred embodiment of strip connector 216 in more detail. Strip connector 216 includes a channel 230 with a flared opening 231 for receiving test strip 10. Tabs 232 and 234 hang over the left and right sides, respectively, of channel 230 at a predetermined height. This predetermined height is set to allow distal end 14 (in thin section 94), but not proximal end 12 (in thick section 96), to be inserted into strip connector 216. In this way, the user may be prevented from improperly inserting test strip 10 into strip connector 216.

Electrical contacts 236 and 238 are disposed in channel 230 behind tabs 232 and 234, and electrical contacts 240-246 are disposed in channel 230 behind electrical contacts 236 and 238. When distal end 14 of test strip 10 is properly inserted into strip connector 216, electrical contacts 236-246 contact electrical contacts 32-38 and auto-on conductor 48 to electrically connect test strip 10 to meter 200. In particular, electrical contacts 236 and 238 contact electrical contacts 32 and 34, respectively, to electrically connect working electrode 22 and counter electrode 24 to meter 200. Electrical contacts 240 and 242 contact electrical contacts 36 and 38, respectively, to electrically fill-detect electrodes 28 and 30 to meter 200. Finally, electrical contacts 244 and 246 electrically connect auto-on conductor 48 to meter 200.

Meter 200 may use data from removable data storage device 220 to calculate glucose levels in blood samples measured by meter 200. Specifically, data storage device 220 may be associated with a lot of test strips and may store one or more parameters that meter 200 may use for that lot. For example, data storage device 220 may store one or more calibration parameters that meter 200 may use to calculate the glucose level from an averaged current measurement. The calibration parameters may include temperature corrections. Data storage device 220 may also store other information related to the lot of test strips and the meter, such as a code identifying the brand of test strips, a code identifying the model of meter to be used, and an expiration date for the lot of test strips. Data storage device 220 may also store other information used by meter 200, such as the duration of the fill timer and the incubation timer, the voltages to use for the "Drop Level 1," "Fill," and "Assay Excitation Level 2" voltages, one or more parameters relating to the number of current measurements to make, and one or more parameters specifying how the meter should average the current measurements, as described in more detail below. Data storage device 220 may also store one or more checksums of the stored data or portions of the stored data.

In a preferred approach, before a given lot of test strips are used with meter 200, the removable data storage device 220 associated with that given lot is first inserted into data connector 218. Meter 200 may then load the relevant data from data storage device 220 into an internal memory when a test strip is inserted into strip connector 216. With the relevant data stored in its internal memory, meter 200 no longer needs data storage device 220 to measure glucose levels using test strips in the given lot. Thus, removable data storage device 220 may be removed from meter 200 and may be used to code other meters. If data storage device 220 is retained in meter 200, meter 200 may no longer access it but instead use the data stored in its internal memory.

Figure 13:
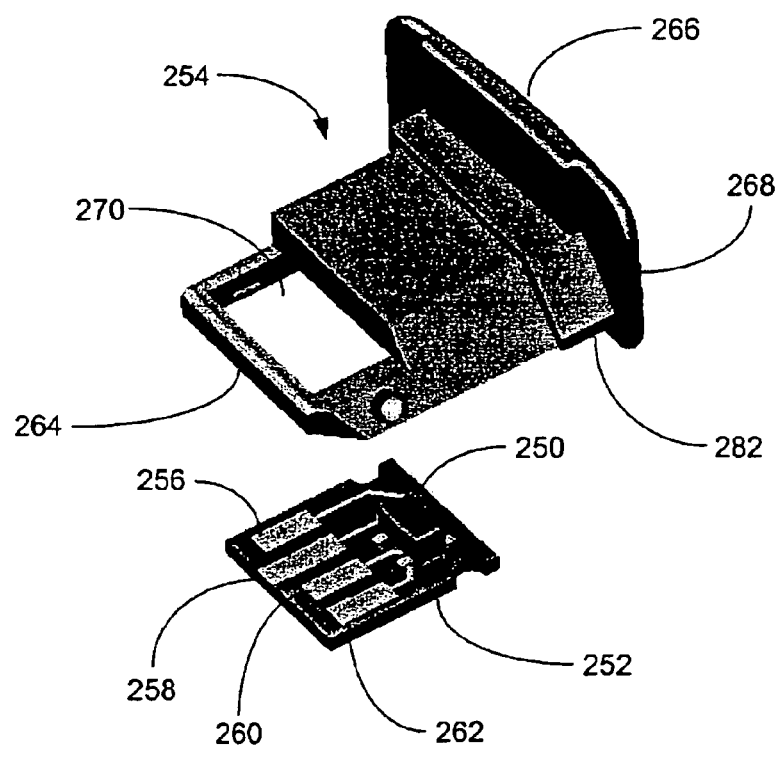
FIG. 13 is an exploded perspective view of the removable data storage device of FIG. 11, in accordance with a preferred embodiment of the present invention.

With reference to FIG. 13, removable data storage device 220 may include a memory chip 250 mounted on a circuit board 252, which, in turn, is mounted to a carrier 254. Memory chip 250 stores the data in a predetermined format. Preferably, memory chip 250 includes a non-volatile memory, so as to retain the stored data when un-powered. For example, memory chip 250 may be an electronically erasable programmable read only memory (EEPROM) chip. Such EEPROM chips can typically be written to many times (e.g., one million write cycles, or more) so that it does not wear out over the life cycle of usage.

Memory chip 250 may be electrically connected to a plurality of electrical contacts on circuit board 252. These electrical contacts may include a voltage supply contact 256, a ground contact 258, a data input/output contact 260, and a clock contact 262. In this way, when the appropriate voltage is applied to voltage supply 256, relative to ground contact 258, data may be synchronously read from or written to memory chip 250 using data input/output contact 260 and clock contact 262. As described in more detail below, ground contact 258 may be longer than the other electrical contacts 256, 260, and 262, for greater reliability.

Carrier 254 may be made out of a material such as plastic and may include a distal end 264 and a proximal end 266. Distal end 264 is intended to be inserted into data connector 218. Proximal end 266 may include a flange 268 to allow a user's fingers to grip removable data storage device 220 for either insertion into or removal from data connector 218. Carrier 254 may include an opening 270 through which electrical contacts 256-262 are accessible. Thus, when data storage device 220 is properly inserted into data connector 218, electrical contacts 256-262 on circuit board 252 contact corresponding electrical contacts 272-278 (shown in FIG. 10), respectively, in data connector 218. In this way, meter 200 may become electrical connected to memory chip 250 to read the data stored therein.

Carrier 254 and data connector 218 may be "keyed" so that removable data storage device 220 may be inserted into connector 218 in only one orientation. For example, carrier 254 may include a wedge-shaped corner 282 and connector 218 may include a wedge-shaped opening 284 for receiving wedge-shaped corner 282. As a result, data storage device 220 may fit into data connector 218 only when oriented so that wedge-shaped corner 282 is received in wedge-shaped opening 284. Beneficially, this keying may cue the user as to the proper insertion orientation and may prevent damage that could be caused by improper insertion.

Another feature of removable data storage device 220 that may enhance its reliability is the greater length of ground contact 258. Specifically, circuit board 252 is mounted to carrier 254 such that ground contact 258 extends closer to distal end 264 (i.e., the end inserted into data connector 218) than the other electrical contacts 256, 260, and 262. As a result, ground contact 258 is the first electrical contact on circuit board 252 to make electrical contact with meter 200 when data storage device 220 is inserted into data connector 218 and the last electrical contact to break electrical contact with meter 200 when data storage device 220 is removed. This prevents memory chip 250 from being powered in an unintended operating mode that may not be reliable, e.g., the supply voltage from meter 200 being applied to memory chip 250 through voltage supply contact 256 without memory chip 250 also being connected to ground through ground contact 258.

4. The Use of the Test Strip with the Meter

Figure 14:
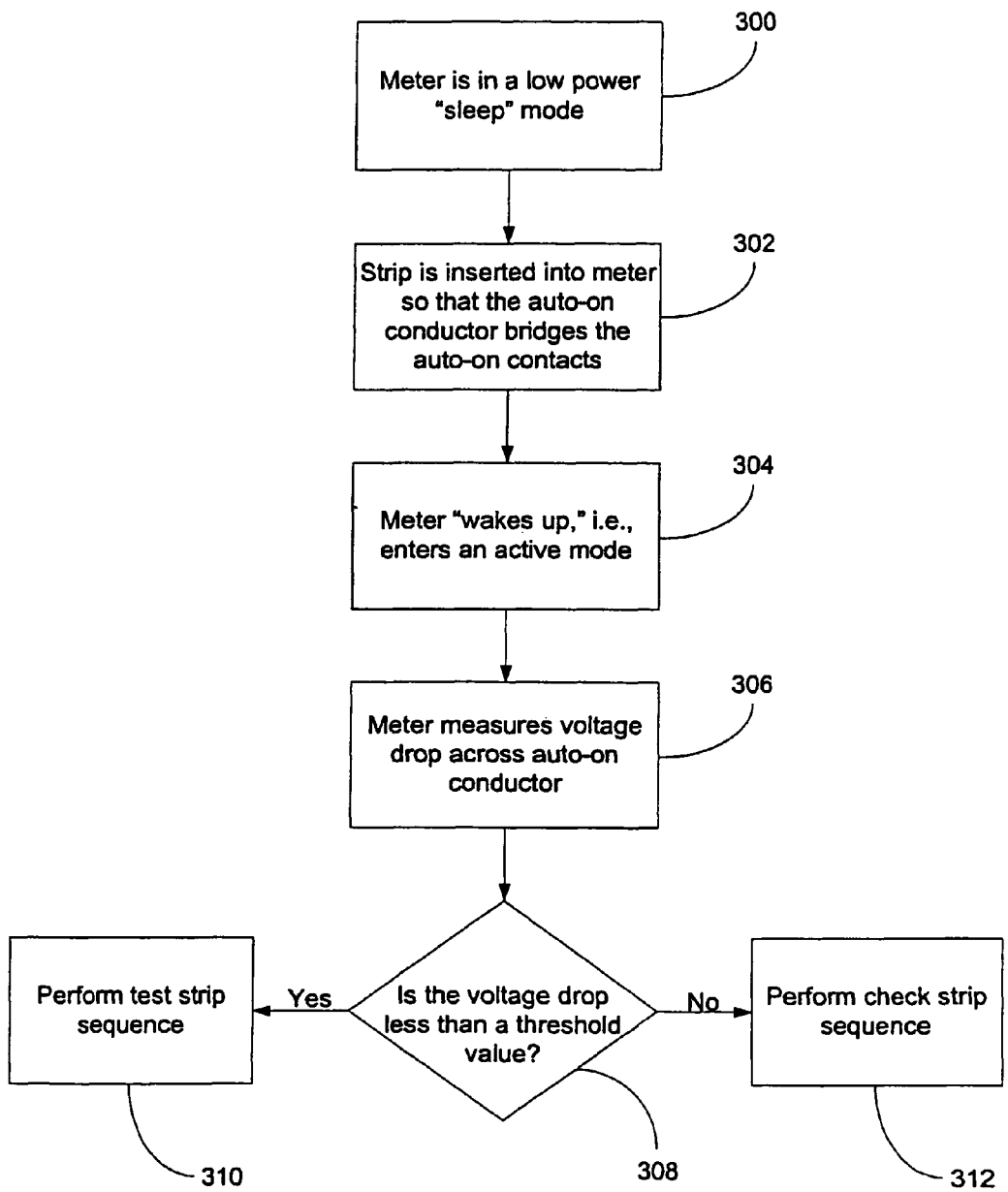
FIG. 14 is a flow chart illustrating a method of using a test strip or a check strip, in accordance with a preferred embodiment of the present invention.

In order to save power, meter 200 is preferably in a low power "sleep" mode most of the time. However, meter 200 may "wake up" and enter an active mode when certain situations occur. For example, actuating one or more of the user controls 222 may cause meter 200 to wake up, as may attempting to use serial port 416 for data transfer. Preferably, inserting either test strip 10 or a check strip into meter 200 also wakes it up. Meter 200 may then determine whether the inserted strip is a test strip or a check strip. The flow chart of FIG. 14 illustrates this process.

At first, meter 200 is in a low power sleep mode, as indicated by step 300. Then, either a test strip or check strip is inserted into meter 200, as indicated by step 302. The insertion causes the auto-on conductor on the strip (e.g., auto-on conductor 48 on test strip 10) to bridge auto-on contacts 244 and 246 in meter 200. As a result, an auto-on current starts to flow through auto-on contacts 244 and 246 and through the auto-on conductor. This auto-on current causes meter 200 to wake up and enter an active mode, as indicated by step 304.

In this active mode, meter 200 measures the voltage drop across the auto-on conductor, as indicated by step 306. In a preferred approach, the resistance of the auto-on conductors in test strips is significantly different than in check strips. Thus, meter 200 may determine whether the strip inserted into it is a test strip or a check strip based on the auto-on voltage drop. For example, the auto-on conductors in test strips may have a substantially lower resistance than in check strips. Accordingly, meter 200 may compare the auto-on voltage drop to a predetermined threshold value, as indicated by step 308. If the auto-on voltage drop is less than the predetermined threshold value, then meter 200 identifies the strip as a test strip and performs a test strip sequence, as indicated by step 310. On the other hand, if the auto-on voltage drop is greater than the predetermined threshold value, then meter 200 identifies the strip as a check strip and performs a check strip sequence, as indicated by step 312.

Figure 15:
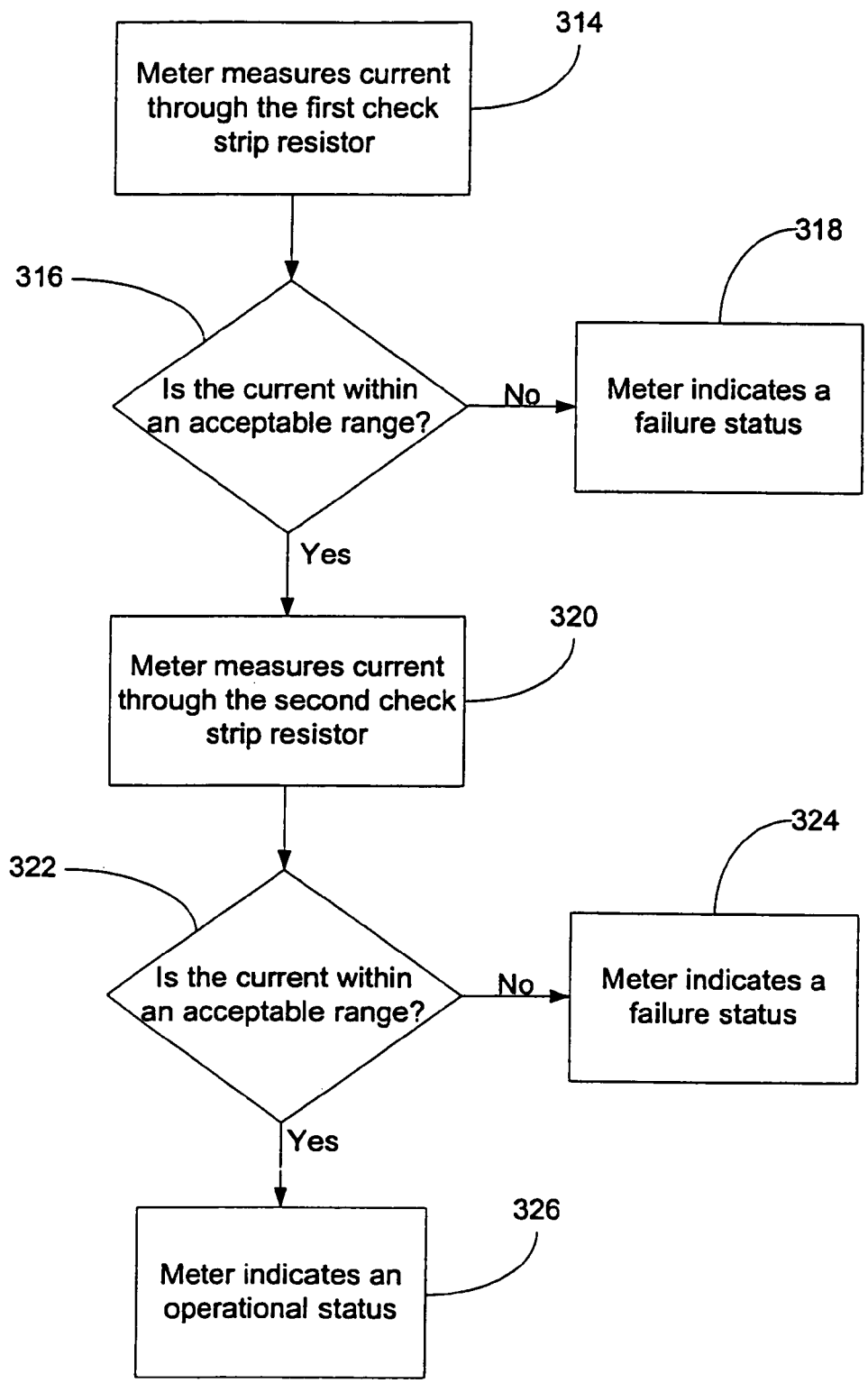
FIG. 15 is a flow chart illustrating a method of using a check strip, in accordance with a preferred embodiment of the present invention.

The flowchart of FIG. 15 illustrates a preferred the check strip sequence. A check strip may have electrical contacts near its distal end (in addition to the auto-on conductor) that are similar to electrical contacts 32-38 on test strip 10, except that the electrical contacts on the check strip may be connected to resistors, with predetermined resistances, rather than to actual electrodes. Thus, when a check strip is inserted into meter 200, electrical contacts 236 and 238 may contact "working electrode" and "counter electrode" contacts on the check strip that are actually connected via a first resistor in the check strip. Similarly, electrical contacts 240 and 242 may contact "fill-detect" contacts on the check strip that are actually connected via a second resistor in the check strip.

As summarized in FIG. 15, meter 200 may perform the check strip sequence by measuring the currents through the first and second resistors in the check strip to determine if the measured values fall within acceptable ranges. If the measured current values do not fall within the acceptable ranges, then there may be a problem with meter 200. Thus, meter 200 may first measure the current through working and counter electrode contacts 236 and 238 to obtain a measured current value through the first resistor, as indicated by step 314. Meter 200 then determines if this measured current value is within the acceptable range, as indicated by step 316. If the measured current value is not within the acceptable range, then meter 200 indicates a failure status, as indicated by step 318. To indicate the failure status, meter 200 may display a message or an icon on display 214 and/or provide some other user-discernible failure indication.

If the measured current through the first resistor is within the acceptable range, then meter 200 may also measure the current through fill-detect electrode contacts 240 and 242 to obtain a measured current value through the second resistor, as indicated by step 320. Then, meter 200 determines whether this measured current value is within an acceptable range, as indicated by step 322. If the measured current value is not within the acceptable range, then meter 200 indicates a failure status, as indicated by step 324. If the measured current value is within the acceptable range, then meter 200 may indicate an operational status. For example, meter 200 may display an "OK" icon on display 214.

Figure 16:
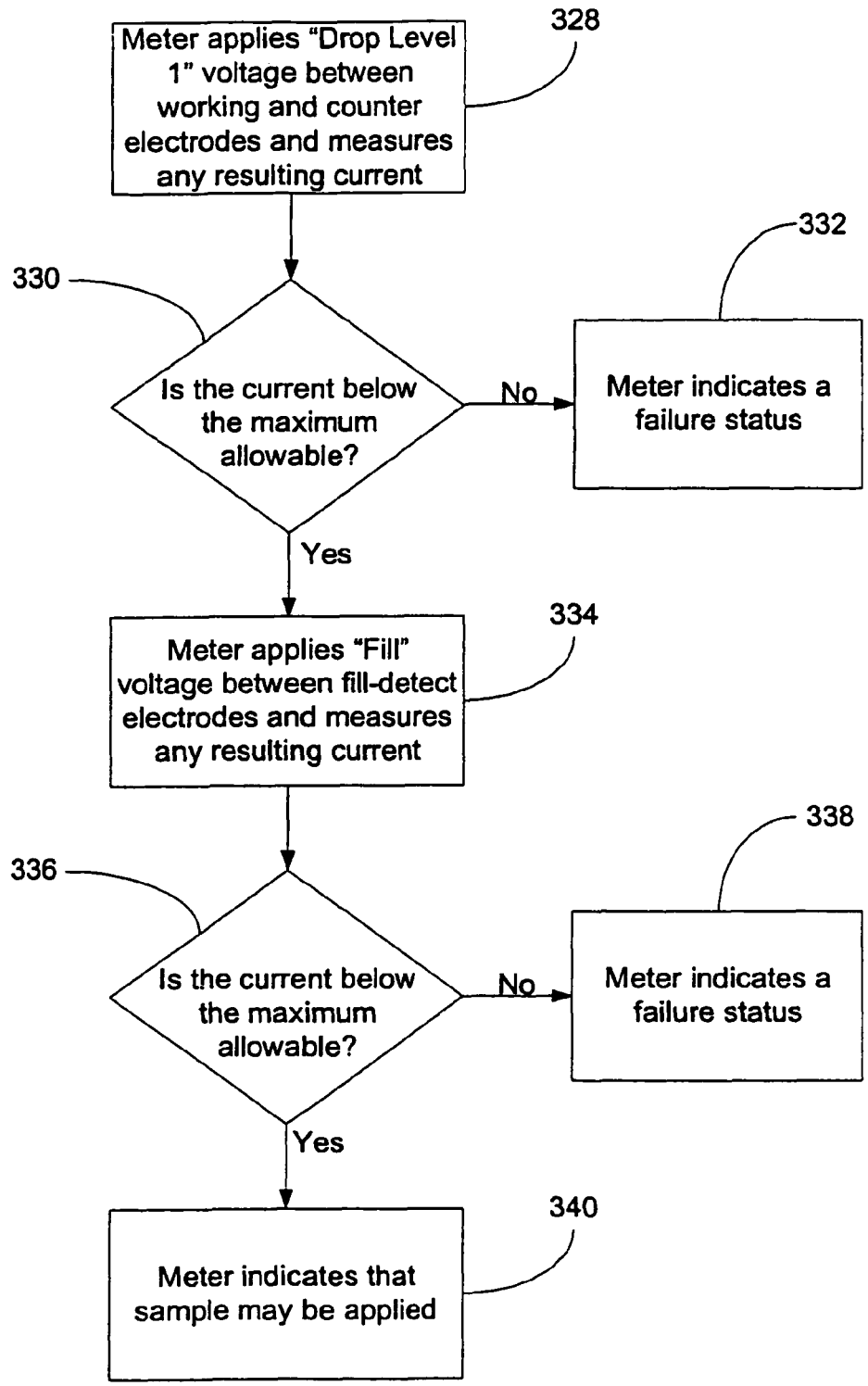
FIG. 16 is a flow chart illustrating a method of using a test strip, in accordance with a preferred embodiment of the present invention.

As noted above, if the meter 200 detects a test strip, then meter 200 performs a test strip sequence. As a first phase of the test strip sequence, meter 200 may validate the working, counter, and fill-detect electrodes by determining whether the impedances between them are sufficiently high. This process is illustrated in the flow chart of FIG. 16.

As indicated by step 328, meter 200 may apply a predetermined first validation voltage, e.g., the "Drop Level 1" voltage, between working and counter electrodes 22 and 24 and measure any resulting current flowing through working electrode 22. The first validation voltage should result in little or no current, because there should not be a low-impedance pathway between working electrode 22 and counter electrode 24. Thus, meter 200 may check whether the resulting current is below a maximum allowable value, as indicated by step 330. If the resulting current is above the maximum value, then meter may indicate a failure status, as indicated by step 332.

Otherwise, meter 200 may proceed with the test strip sequence and apply a predetermined second validation voltage, e.g., the "Fill" voltage, across fill-detect electrodes 28 and 30 and measure any resulting current flowing through fill-detect anode 28, as indicated by step 334. The second validation voltage should also result in little or no current, because there should not be any low-impedance pathways between any of the electrodes. Thus, meter 200 may check whether the resulting current is below a maximum allowable value, as indicated by step 336. If the resulting current is above this maximum value, then meter may indicate a failure status, as indicated by step 338. Otherwise, meter 200 may indicate that a blood sample may be applied to test strip 10. For example, meter 200 may display a message or an icon on display 214 and/or provide some other user-discernible indication.

Meter 200 may perform the measurement of step 334 at the same time it performs the measurement of step 328. Thus, meter 200 may apply the "Drop Level 1" voltage between working and counter electrodes 22 and 24, measuring any resulting current through working electrode 22, while at the same time applying the "Fill" voltage between fill-detect electrodes 28 and 30 and measuring any resulting current through fill-detect anode 28.

Figure 17:
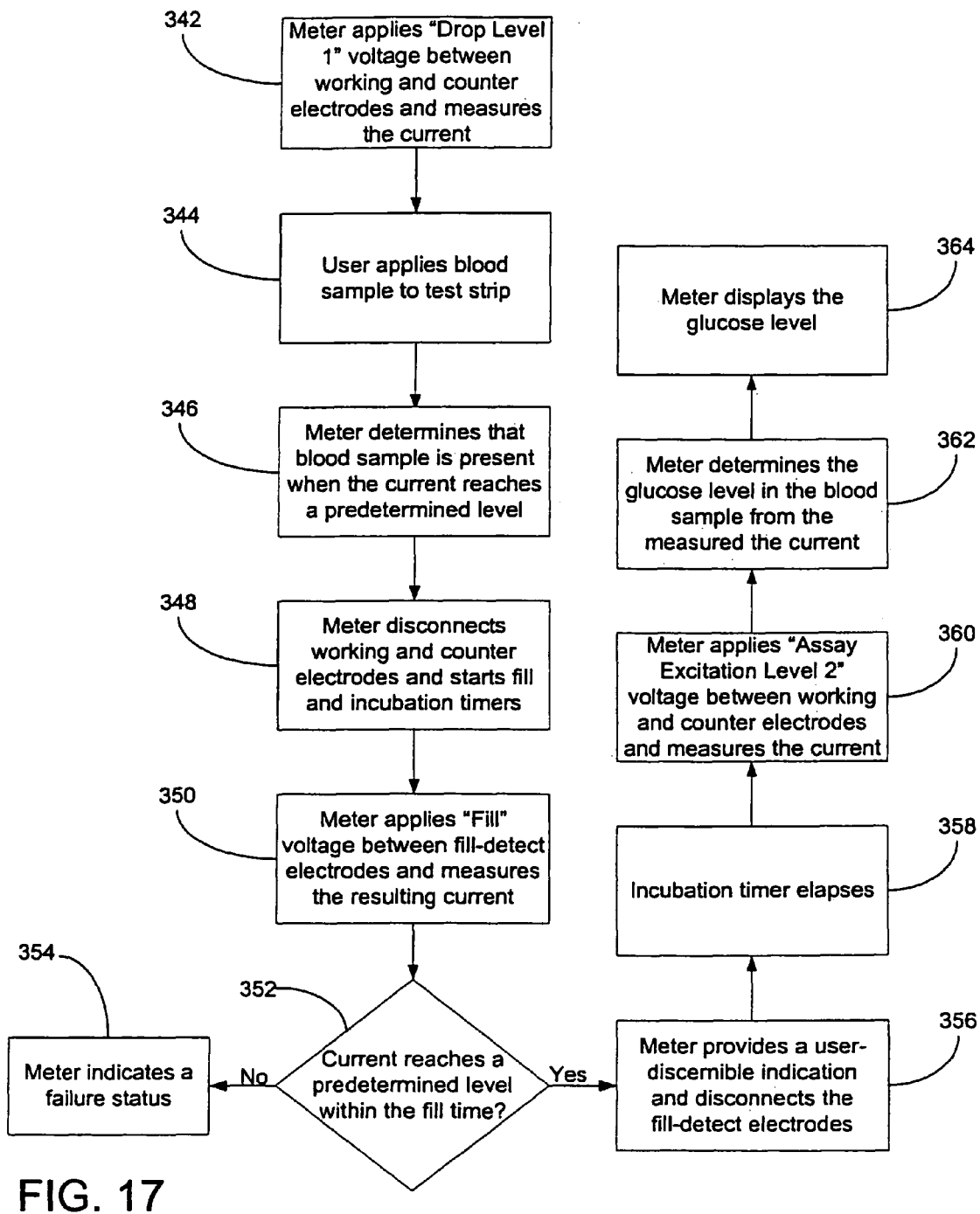
FIG. 17 is a flow chart illustrating a method of using a test strip, in accordance with a preferred embodiment of the present invention.

If the electrodes are validated, meter 200 may then proceed with the process illustrated in the flow chart of FIG. 17. To detect when the user applies the blood sample, meter 200 applies "Drop Level 1" voltage across working electrode 22 and counter electrode 24 and measures any resulting current flowing between these electrodes, as indicated by step 342. Preferably, the "Drop Level 1" voltage is less than the redox potential of the chemistry used in reagent layer 90. At step 344, the user applies a blood sample to test strip 10. More particularly, the user applies the blood sample to the opening of sample chamber 88 at proximal end 12, as shown in FIG. 3. As noted above, sample chamber 88 is dimensioned to draw the blood sample into it by capillary action. As the blood sample moves into sample chamber 88, it will eventually bridge working electrode 22 and counter electrode 24, thereby providing an electrically conductive pathway between them. Thus, meter 200 determines that a blood sample is present in sample chamber 88 when the resulting current reaches a predetermined threshold value or series of threshold values with an overall positive magnitude change, as indicated by step 346. When meter 200 detects the blood sample in this way, meter 200 disconnects working and counter electrodes 22 and 24 putting them in a high impedance state relative to fill-detect electrodes 28 and 30, and meter 200 starts a fill timer and an incubation timer, as indicated by step 348. Before meter 200 puts working and counter electrodes 22 and 24 in the high impedance state, meter 200 may first ground them to discharge stored charges.

The fill timer sets a time limit for the blood sample to traverse reagent layer 90 and reach fill-detect electrodes 28 and 30. The incubation timer sets a delay period to allow the blood sample to react with reagent layer 90. Once meter 200 starts the fill timer running, meter 200 applies a voltage, the "Fill" voltage, between fill-detect electrodes 28 and 30 and measures the resulting current flowing between these electrodes, as indicated by step 350. As indicated by step 352, meter 200 checks whether the resulting current reaches a predetermined threshold value or a series of thresholds with an overall positive magnitude change before the fill timer elapses. Preferably, the current threshold(s) are set so that meter 200 can determine whether sufficient sample has reached fill-detect electrodes 28 and 30 and whether the sample has become mixed with the chemical constituents in reagent layer 90.

If the current does not reach the required value, then there may be some problem with test strip 10. For example, there may be a blockage in sample chamber 88. There may be an inadequate amount of sample. There may be no reagent layer, or the chemical constituents reagent layer may have failed to mix with the blood sample. Any of these problems may make the glucose measurement unreliable. Accordingly, if the fill timer elapses without a sufficient current through fill-detect electrodes 28 and 30, meter 200 may indicate a failure status, as indicated by step 354. Meter 200 may indicate this failure status by displaying an error message or icon on display 214 and/or by providing some other user-discernible indication. The duration of the fill timer may, for example, be in the range of 2 to 6 seconds.

If however, meter 200 detects sufficient current through fill-detect electrodes 28 and 30 before the fill timer elapses, then meter 200 may proceed with the glucose measurement process. As indicated by step 356, meter 200 may provide an indication to the user that meter 200 has detected adequate sample mixed with the chemical constituents of reagent layer 90. For example, meter 200 may beep, display a message or icon on display 214, or provide some other user-discernible indication. Preferably, meter 200 also disconnects fill-detect electrodes 28 and 30, bringing them to a high impedance state relative to working electrode 22 and counter electrode 24. Meter 200 may ground fill-detect electrodes 28 and 30 before putting them into the high impedance state in order to discharge stored charges. Meter 200 then waits for the incubation timer to elapse, as indicated by step 358, in order to allow sufficient time for the blood sample to react with reagent layer 90. The incubation timer may, for example, take about 2 seconds to about 10 seconds to elapse, depending on the implementation. In a preferred embodiment, the incubation timer lasts about 5 seconds.

When the incubation timer elapses, meter 200 applies the "Assay Excitation Level 2" voltage between working electrode 22 and counter electrode 24 and measures the resulting current flowing between these electrodes, as indicated by step 360. Preferably, meter 200 measures the resulting current at a fixed sampling rate throughout a measurement period, to obtain a plurality of current measurements. The measurement period may last from about 5 seconds to about 15 seconds, depending on the implementation. In a preferred embodiment, the measurement period lasts about 5 seconds.

Meter 200 then determines the glucose level in the blood sample from the current measurements, as indicated by step 362. In a preferred approach, meter 200 may average the current measurements to obtain an average current value at a predetermined point of time during the measurement period. Meter 200 may then use the calibration data obtained from removable data storage device 220 and stored in its internal memory to calculate the glucose level from the average current value. Meter 200 may also take a temperature reading and use the temperature reading to correct the measured glucose level for temperature dependence. In addition, meter 200 may check the validity of the current measurements by checking that the measured current decreases over time, as expected.

For example, in a preferred embodiment, meter 200 may take a predetermined number of current measurements $(m_1 \ldots m_M)$ in 0.1 second time intervals. The predetermined number, M, may, for example, range from 50 to 150, and it may be a parameter specified in removable data storage device 220. The meter may then average every n current measurements to provide a plurality of data points $(d_1 \ldots d_N)$. Thus, if n is equal to 3, the meter would calculate $d_1$ by averaging $m_1$, $m_2$, and $m_3$, and would calculated $d_2$ by averaging $m_2$, $m_3$, and $m_4$. The averaging parameter, n, may be a parameter specified in removable data storage device 220. One of the data points may then be selected as the center point for another level of averaging, in which the meter averages together the data points around and including the center point to provide a meter reading, X. Thus, if $d_2$ is selected as the center point, then the meter may average $d_1$, $d_2$, and $d_3$ together to calculate the meter reading, X. Removable data storage device 220 may store a parameter that specifies which of the data points to use as the center point for calculating the meter reading, X. Meter 200 then calculates the glucose level, Y, from the meter reading, X, and one or more calibration parameters, which may be specified in removable data storage device 220. For example, in a preferred embodiment, meter 200 may use three calibration parameters, a, b, and c, to calculate Y from the expression a+bX+c/X.

The calculated glucose level, Y, may not be temperature corrected, however. To correct for temperature, meter 200 may apply one or more temperature correction parameters, which may be specified in removable data storage device 220. For example, in a preferred embodiment, the temperature-corrected glucose level may be calculated from the expression A+BT+CYT+DY, where A, B, C, and D are temperature correction parameters and T is a measured temperature. The calibration parameters A, B, C, and D may be specified in removable data storage device 220. In other embodiments, the temperature correction may use only a single parameter, S, which may be specified in removable data storage device 220. For example, the temperature-corrected glucose level may be calculated from the expression $Y/[(1+S(T-21)]$.

If the current measurements appear valid, then meter 200 displays the glucose level, typically as a number, on display 214, as indicated by step 364. Meter 200 may also store the measured glucose level, with a timestamp, in its internal memory.

5. Meter Electronics

Figure 18:
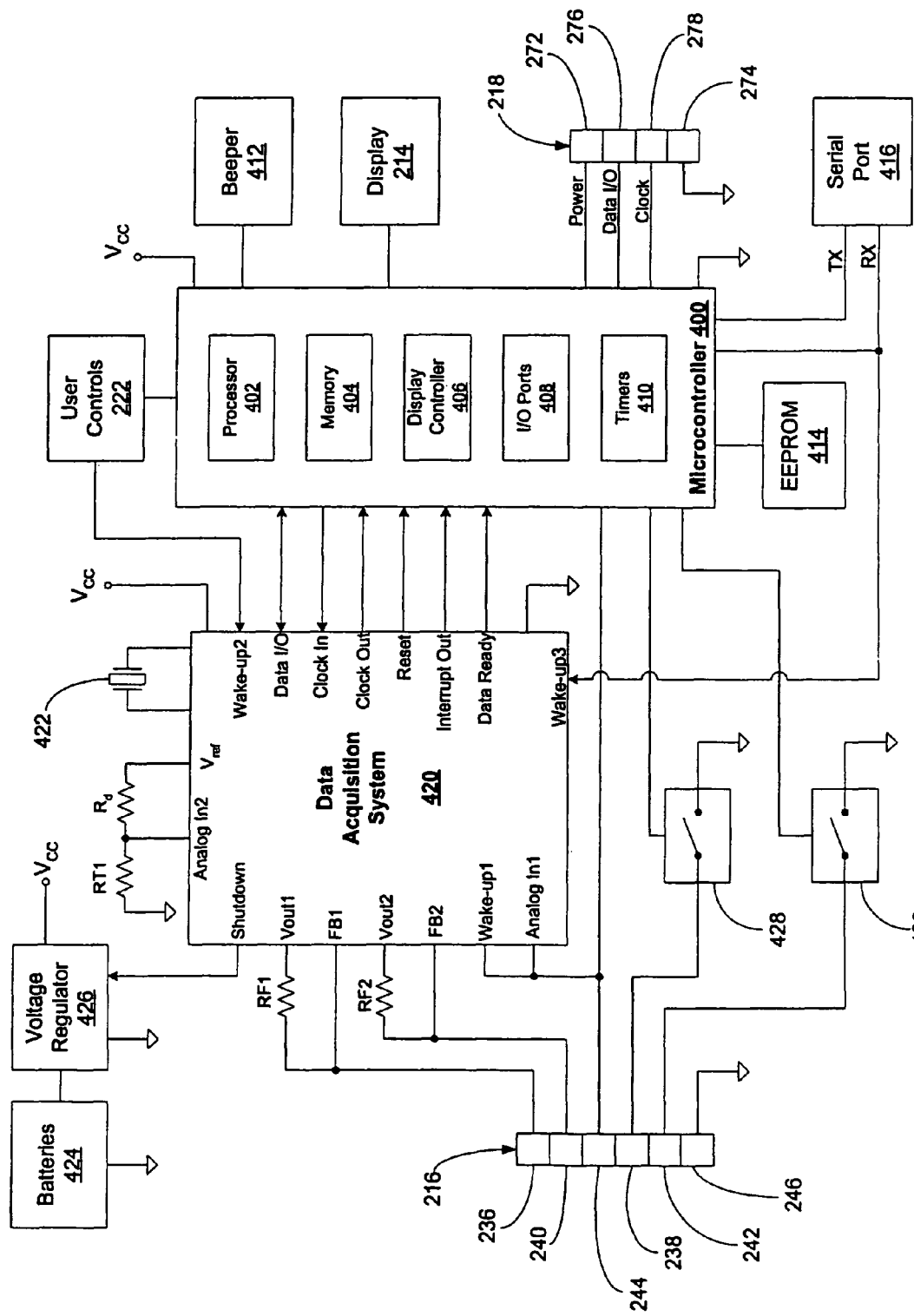
FIG. 18 is a simplified schematic diagram of the electronics of the meter of FIG. 10, in accordance with a preferred embodiment of the present invention.

FIG. 18 shows, in simplified form, the electronic components of meter 200, in accordance with a preferred embodiment. Meter 200 may include a microcontroller 400 that controls the operation of meter 200 in accordance with programming, which may be provided as software and/or firmware. Microcontroller 400 may include a processor 402, a memory 404, which may include read-only memory (ROM) and/or random access memory (RAM), a display controller 406, and one or more input/output (I/O) ports 408. Memory 404 may store a plurality of machine language instructions that comprises the programming for controlling the operation of meter 200. Memory 404 may also store data Processor 402 executes the machine language instructions, which may be stored in memory 404 or in other components, to control microcontroller 400 and, thus, meter 200. In particular, processor 402 executes the stored machine language instructions so that meter 200 performs the functions summarized in the flowcharts of FIGS. 14-17 and described above.

Microcontroller 400 may also include other components under the control of processor 402. For example, microcontroller 400 may include a display controller 406 to help processor 402 control display 214. In a preferred embodiment, display 214 is an LCD and display controller 406 is an LCD driver/controller. Microcontroller may also include I/O ports 408, which enable processor 402 to communicate with components external to microcontroller 400. Microcontroller 400 may also one or more timers 410. Processor 402 may use timers 410 to measure the fill time period, incubation time period, and other time periods described above. Microcontroller 400 may be provided as an integrated circuit; such as the HD64F38024H, available from Hitachi.

Microcontroller 400 is preferably connected to components that provide a user interface. The components that make up the user interface of meter 200 may include display 214, a beeper 412, and user controls 222. Microcontroller 400 may display text and/or graphics on display 214. Microcontroller may cause beeper 412 to beep, such as to indicate that adequate sample (mixed with the chemistry of reagent layer 90) has reached fill-detect electrodes 28 and 30, as described above. Microcontroller 400 may also be connected to other components, such as one or more light-emitting diodes (LEDs), to provide user-discernible indications, which may be visible, audible, or tactile. Microcontroller 400 may receive user input from user controls 222. In a preferred embodiment, user controls 222 consists of a plurality of discrete switches. However, user controls 222 may also include a touch screen or other components with which a user can provide input to meter 200.

Microcontroller 400 may have access to one or more memories external to it, such as an EEPROM 414. In a preferred embodiment, microcontroller 400 stores the measured glucose levels, and the times and dates the glucose measurements occurred, in EEPROM 414. By using user controls 222, the user may also be able to cause microcontroller 400 to display one or more of the glucose measurements stored in EEPROM 414 on display 214. Microcontroller 400 may also be connected to a serial port 416, through which the user can access the glucose measurements stored in EEPROM 414. Microcontroller 400 may use a transmit line, "TX," to transmit signals to serial port 416 and may use a receive line, "RX," to receive signals from serial port 416.

EEPROM 414 may also store the data from removable data storage device 220. In this regard, FIG. 18 shows how electrical contacts 272-278 of data connector 216 are connected inside of meter 200. Contact 272 is connected to a source of power, which may be through microcontroller 400. In this way, microcontroller 400 can do "power management," powering removable data storage 220, through contact 272, only when necessary, e.g., when downloading data from removable data storage device 220. Contact 274 is connected to ground. Contacts 276 and 278 are connected to data input/output and clock outputs, respectively, of microcontroller 400. In this way, microcontroller 400 may download the data from data storage device 220, when connected to data connector 216, and store the data in EEPROM 414.

In a preferred embodiment, meter 200 also includes a data acquisition system (DAS) 420 that is digitally interfaced with microcontroller 400. DAS 420 may be provided as an integrated circuit, such as the MAX1414, available from Maxim Integrated Products, Sunnyvale, Calif.

DAS 420 includes one or more digital-to-analog converters (DACs) that generate analog voltages in response to digital data from microcontroller 400. In particular, DAS 420 includes "Vout1" and "FB1" terminals, which DAS 420 uses to apply analog voltages generated by a first DAC to working electrode 22, when test strip 10 is inserted in strip connector 216. Similarly, DAS 420 includes "Vout2" and "FB2" terminals, which DAS 420 uses to apply analog voltages generated by a second DAC to fill-detect anode 28, when test strip 10 is inserted in strip connector 216. The one or more DACs in DAS 420 generate analog voltages based on digital signals provided by microcontroller 400. In this way, the voltages generated by the one or more DACs may be selected by processor 402.

DAS 420 also includes one or more analog-to-digital converters (ADCs) with which DAS 420 is able to measure analog signals. As described in more detail below, DAS 420 may use one or more ADCs connected to the "Vout1" and "Vout2" terminals to measure currents from working electrode 22 and counter electrode 24, respectively, when test strip 10 is inserted in strip connector 216. DAS 420 may also include one or more other terminals through which the ADCs may measure analog signals, such as the "Analog In1" and "Analog In2" terminals shown in FIG. 18. DAS 420 may use the "Analog In1" terminal to measure the voltage across the auto-on conductor in a test strip or check strip that is connected to strip connector 216. The "Analog In2" terminal may be connected to a thermistor, RT1, to enable DAS 420 to measure temperature. In particular, DAS 420 may supply a reference voltage, $V_{ref}$, through a voltage divider that includes thermistor, RT1, and another resister, $R_d$. DAS 420 may use the "Analog In2" terminal to measure the voltage across thermistor, RT1. DAS 420 transfers the digital values obtained from the one or more ADCs to microcontroller 400, via the digital interface between these components.

Preferably, DAS 420 has at least two modes of operation, a "sleep" or low-power mode and an "active" or run mode. In the active mode, DAS 420 has full functionality. In the sleep mode, DAS 420 has reduced functionality but draws much less current. For example, while DAS 420 may draw 1 mA or more in the active mode, DAS 420 may draw only microamps in the sleep mode. As shown in FIG. 18, DAS 420 may include "Wake-up1," "Wake-up2," and "Wake-up3" inputs. When appropriate signals are asserted at any of these "Wake-up" terminals, DAS 420 may wake up from the sleep mode, enter the active mode, and wake up the rest of meter 200, as described in more detail below. In a preferred embodiment, the "Wake-up" inputs are active-low inputs that are internally pulled up to the supply voltage, $V_{cc}$. As described in more detail below, inserting the auto-on conductor in either a test strip or check strip into strip connector 216 causes the "Wake-up1" input to go low and, thereby, causing DAS 420 to enter the active mode. In addition, the "Wake-up2" input may be connected to one or more of user controls 222. In this way, the user's actuation of at least certain of user controls 222 causes DAS 420 to enter the active mode. Finally, the "Wake-up3" input may be connected to serial port 416, e.g., via receive line, "RX." In this way, attempting to use serial port 416 for data transfer may wake up DAS 420 and, hence, meter 200.

As shown in FIG. 18, DAS 420 includes several terminals that are connected to microcontroller 400. DAS 420 includes one or more "Data I/O" terminals, through which microcontroller 400 may write digital data to and read digital data from DAS 420. DAS 420 also includes a "Clock In" terminal that receives a clock signal from microcontroller 400 to coordinate data transfer to and from the "Data I/O" terminals. DAS 420 may also include a "Clock Out" terminal through which DAS 420 may supply a clock signal that drives microcontroller 400. DAS 420 may generate this clock signal by using a crystal 422. DAS 420 may also generate a real time clock (RTC) using crystal 422.

DAS 420 may also include other terminals through which DAS 420 may output other types of digital signals to microcontroller 400. For example, example DAS 420 may include a "Reset" terminal, through which DAS 420 may output a signal for resetting microcontroller 400. DAS 420 may also include one or more "Interrupt Out" terminals, which DAS 420 may use to provide interrupt signals to microcontroller 400. DAS 420 may also include one or more "Data Ready" inputs that DAS 420 may use to signal microcontroller 400 that DAS 420 has acquired data, such as from an analog-to-digital conversion, which is ready to be transferred to microcontroller 400.

As shown in FIG. 18, meter 200 may include a power source, such as one or more batteries 424. A voltage regulator 426 may provide a regulated supply voltage, $V_{cc}$, from the voltage supplied by batteries 424. The supply voltage, $V_{cc}$, may then power the other components of meter 200. In a preferred embodiment, voltage regulator 426 is a step-up DC-to-DC voltage converter. Voltage regulator 426 may be provided as an integrated circuit and other components, such as an inductor, capacitors, and resistors. The integrated circuit may, for example, be a MAX1724, available from Maxim Integrated Products, Sunnyvale, Calif.

Preferably, voltage regulator 426 has a shutdown mode, in which it provides only an unregulated output voltage. DAS 420 may include a "Shutdown" terminal through which DAS 420 may control voltage regulator 426. In particular, when DAS 420 enters the sleep mode, DAS 420 may assert a low level signal at its "Shutdown" terminal, causing voltage regulator 426 to enter the shutdown mode. When DAS 420 enters the active mode, it asserts a high level signal at its "Shutdown" terminal, allowing voltage regulator 426 to operate normally.

FIG. 18 also shows how electrical contacts 236-246 of strip connector 216 are connected in meter 200. Contacts 236 and 238, which are electrically connected to working electrode 22 and counter electrode 24, respectively, when test strip 10 is inserted in strip connector 216, are connected as follows. Contact 236, for working electrode 22, is connected to the "FB1" terminal of DAS 420 and connected via a resistor, RF1, to the "Vout1" terminal of DAS 420. Contact 238, for counter electrode 24, is connected to a switch 428. Switch 428 allows contact 238 (and, hence, counter electrode 24) to be connected to ground or left in a high impedance state. Switch 428 may be digitally controlled by microcontroller 400, as shown in FIG. 18. With counter electrode 24 connected to ground, DAS 420 may use the "Vout1" and "FB1" terminals to apply voltages to working electrode 22 (relative to counter electrode 24) and to measure the current through working electrode 22.

Contacts 240 and 242, which are electrically connected to fill-detect anode 28 and fill-detect cathode 30, respectively, when test strip 10 is inserted in strip connector 216, are connected as follows. Contact 240, for fill-detect anode 28, is connected to the "FB2" terminal of DAS 420 and connected via a resistor, RF2, to the "Vout2" terminal of DAS 420. Contact 242, for fill-detect cathode 30, is connected to a switch 430. Switch 430 allows contact 242 (and, hence, fill-detect cathode 30) to be connected to ground or left in a high impedance state. Switch 430 may be digitally controlled by microcontroller 400, as shown in FIG. 18. With fill-detect cathode 30 connected to ground, DAS 420 may use the "Vout2" and "FB2" terminals to apply voltages to fill-detect anode 28 (relative to fill-detect cathode 30) and to measure the current through fill-detect anode 28.

Switches 428 and 430 may be single-pole/single-throw (SPST) switches, and they may be provided as an integrated circuit, such as the MAX4641, available from Maxim Integrated Products, Sunnyvale, Calif. However, other configurations for switches 428 and 430 could be used.

Contacts 244 and 246, which are electrically connected to the auto-on conductor when a test strip or check strip is inserted into strip connector 216, are connected as follows. Contact 246 is connected to ground or other reference potential. Contact 244 is connected to the "Analog In1" and "Wake-up1" terminals of DAS 420 and to microcontroller 400. As described in more detail below, the presence of the auto-on conductor drives the "Wake-up1" terminal low, thereby waking up DAS 420 and causing it to enter an active mode. DAS 420 uses the "Analog In1"terminal to measure the voltage across the auto-on conductor. By virtue of its connection to contact 244, microcontroller 400 is able to determine whether the auto-on conductor is present, and, thus, whether either a test strip or check strip is connected to strip connector 216.

Figure 19:
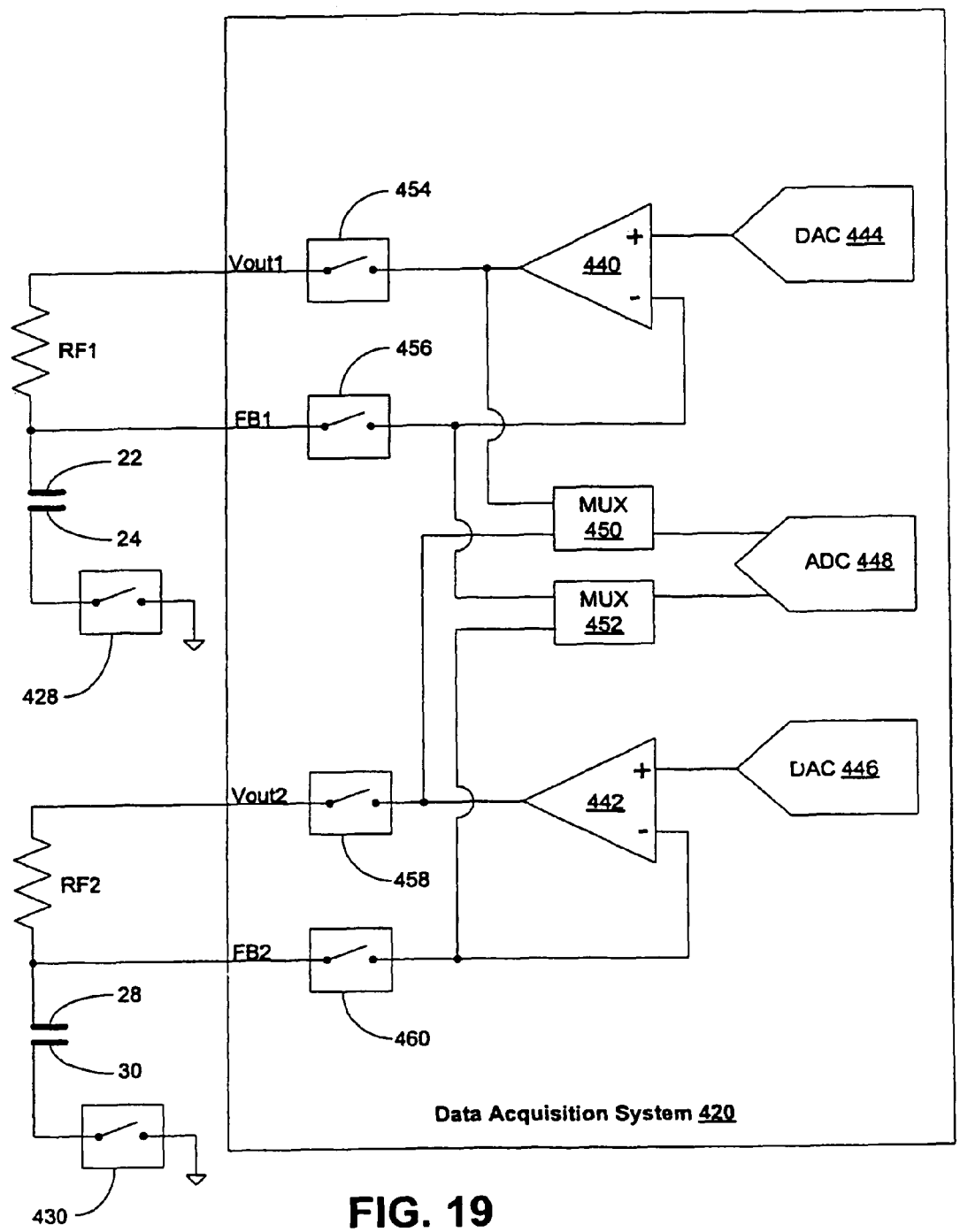
FIG. 19 is a simplified schematic diagram of the electrical connections between the meter of FIG. 10 and the electrodes of the test strip of FIG. 1, in accordance with a preferred embodiment of the present invention.

FIG. 19 shows in greater detail the functional aspects of the connections between meter 200 and electrodes 22, 24, 28, and 30, when test strip 10 is inserted in strip connector 216. As shown in FIG. 19, DAS 420 functionally includes an amplifier 440 for working electrode 22 and an amplifier 442 for fill-detect anode 28. More particularly, the output of amplifier 440 is connected to working electrode 22, via the "Vout1" terminal and resistor, RF1, and the inverting input of amplifier 440 is connected to working electrode 22, via the "FB1" terminal. Similarly, the output of amplifier 442 is connected to fill-detect anode 28, via the "Vout2" terminal and resistor, RF2, and the inverting input of amplifier 442 is connected to fill-detect anode 28, via the "FB2" terminal.

To generate selected analog voltages to apply to working electrode 22 and fill-detect electrode 28, DAS 420 includes a first DAC 444 and a second DAC 446, respectively. DAC 444 is connected to the non-inverting input of amplifier 440, and DAC 446 is connected to the non-inverting input of amplifier 442. In this way, amplifier 440 applies a voltage to the "Vout1" terminal, such that the voltage at working electrode 22, as sensed at the inverting input of amplifier 440, is essentially equal to the voltage generated by DAC 444. Similarly, amplifier 442 applies a voltage to the "Vout2" terminal, such that the voltage at fill-detect electrode 28, as sensed at the inverting input of amplifier 442, is essentially equal to the voltage generated by DAC 446.

To measure the currents through working electrode 22 and fill-detect anode 28, DAS 420 includes an ADC 448 and multiplexers (MUXes) 450 and 452. MUXes 450 and 452 are able to select the inputs of ADC 448 from among the "Vout1," "FB1," "Vout2," and "FB2" terminals. DAS 420 may also include one or more buffers and/or amplifiers (not shown) between ADC 448 and MUXes 450 and 452. To measure the current through working electrode 22, MUXes 450 and 452 connect ADC 448 to the "Vout1" and "FB1" terminals to measure the voltage across resistor, RF1, which is proportional to the current through working electrode 22. To measure the current through fill-detect electrode 28, MUXes 450 and 452 connect ADC 448 to the "Vout2" and "FB2" terminals to measure the voltage across resistor, RF2, which is proportional to the current through fill-detect anode 28.

As noted above, meter 200 preferably includes switches 428 and 430 that may be used to bring counter electrode 24 and fill-detect cathode 30, respectively, into a high impedance state. It is also preferable for meter 200 to be able to bring working electrode 22 and fill-detect anode 28 into a high impedance state as well. In a preferred embodiment, this may be achieved by DAS 420 being able to bring terminals "Vout1," "FB1," "Vout2," and "FB2" into high impedance states. Accordingly, DAS 420 may effectively include switches 454, 456, 458, and 460, as shown in FIG. 19. Although switches 428, 430, and, 454-460 may be SPST switches, as shown in FIG. 19, other types of switches, such as single pole-double throw (SPDT) switches, may be used, and the switches may be arranged in other ways, in order to provide meter 200 with the ability to select one pair of electrodes (either the working and counter electrode pair or the fill-detect electrode pair) and leave the other pair of electrodes in a high impedance state. For example, a pair of SPDT switches may be used, with one SPDT switch selecting which of working electrode 22 and fill-detect 28 to connect to DAS 420 and the other SPDT switch selecting which of counter electrode 24 and fill-detect cathode to connect to ground. In other cases, meter 200 may not be configured to bring all of the electrodes into high impedance states. For example, in some embodiments, meter 200 may not include switch 428, with the result that counter electrode 24 is always connected to ground when test strip 10 is inserted in strip connector 216.

Figure 20:
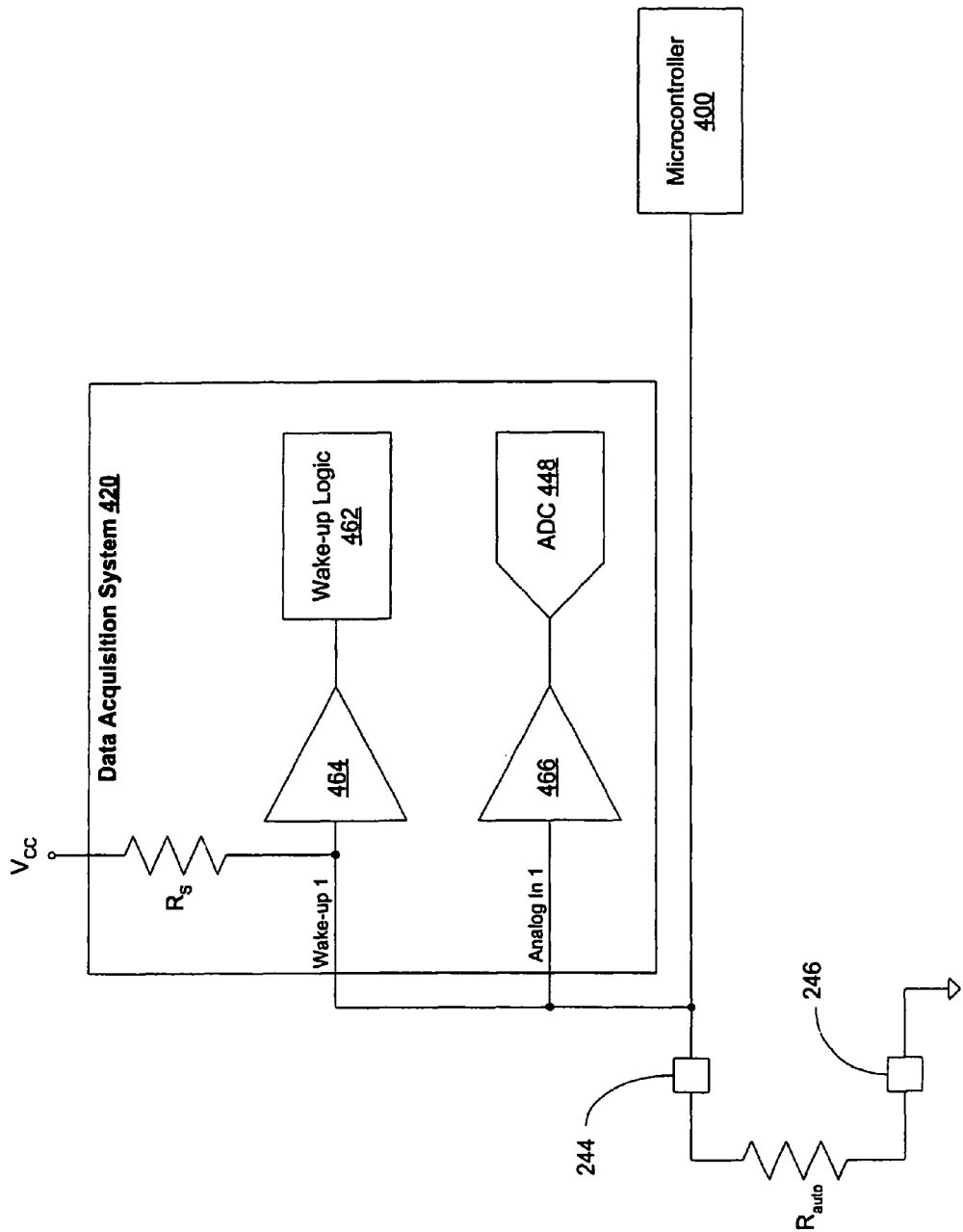
FIG. 20 is a simplified schematic diagram of the electrical connections between the meter of FIG. 10 and the auto-on conductor of the test strip of FIG. 1, in accordance with a preferred embodiment of the present invention.

FIG. 20 shows in greater detail the functional aspects of the connections between meter 200 and the auto-on conductor when either a test strip or a check strip is inserted in strip connector 216. As shown in FIG. 20, the auto-on conductor provides an effective resistance, $R_{auto}$, between contacts 244 and 246 of strip connector 216. Within meter 200, contact 244 is connected to the source voltage, $V_{cc}$, through an effective resistance, $R_s$. For example, the "Wake-up1" terminal of DAS 420, to which contact 244 is connected, may be internally pulled up to $V_{cc}$, through an effective resistance, $R_s$. Accordingly, when either a test strip or a check strip is inserted into strip connector 216, such that the auto-on conductor bridges contacts 244 and 246, a current flows through the auto-on resistor and a voltage drop develops between contacts 244 and 246. The magnitude of this auto-on voltage drop depends on the relative magnitudes of $R_{auto}$ and $R_s$. Preferably, $R_{auto}$ is chosen sufficiently low for the test strips and check strips, relative to $R_s$, such that the auto-on voltage is less than the logic low voltage (which may be about 0.8 volts) used in meter 200. It is also preferable for $R_{auto}$ to be substantially different in test strips and check strips, so that meter 200 may determine the strip type from the auto-on voltage drop. For example, if $R_s$ is about 500 kΩ, then $R_{auto}$ may be less than about 20 Ω in a test strip and may be approximately 20 kΩ in a check strip. In this way, microcontroller 400 may determine that either a test strip or check strip is inserted in strip connector 216 by sensing a logic low voltage at contact 244.

DAS 420 also senses the auto-on voltage drop and uses it to wake up meter 200 and to determine the strip type, i.e., whether a test strip or a check strip has been inserted into strip connector 216. In the case of a test strip, DAS 420 may also confirm that the test strip has been properly inserted into strip connector 216.

DAS 420 may include wake-up logic 462, which senses the voltage at the "Wake-up1" terminal, via one or more buffers and/or amplifiers, such as buffer 464. DAS 420 also includes ADC 448, which can measure the voltage at the "Analog In1" terminal, via one or more buffers and/or amplifiers, such as buffer 466. Although not shown in FIG. 20, MUXes 450 and 452 may be connected between buffer 466 and ADC 448.

When no strip is present in strip connector 216, contact 244 (and, thus, the "Wake-up1" terminal) is at a high voltage, at or near $V_{cc}$. However, when either a test strip or a check strip is inserted in strip connector 216, the auto-on conductor drives the voltage at the "Wake-up1" terminal low, as described above. Wake-up logic 462 senses the voltage at the "Wake-up1" terminal going low and, in response, initiates a wake-up sequence to bring DAS 420 into an active mode. As part of this wake-up sequence, wake-up logic 462 may cause DAS 420 to assert a signal at its "Shutdown" terminal to turn on voltage regulator 426. Wake-up logic 462 may also cause DAS 420 to generate signals to wake up microcontroller 400. For example, wake-up logic 462 may cause DAS 420 to assert a clock signal through its "Clock Out" terminal, a reset signal through its "Reset" terminal, and an interrupt signal through its "Interrupt Out" terminal to activate microcontroller 400.

Though not shown in FIG. 20, wake-up logic 462 may also sense the voltages at the "Wake-up1" and "Wake-up2" terminals and, in response to a voltage at one of these terminals going low, may initiate a wake-up sequence similar to that described above.

When DAS 420 enters the active mode, it also determines the type of strip inserted into strip connector 216. In particular, ADC 448 measures the voltage at the "Analog In1" terminal. DAS 420 then reports the measured voltage to microcontroller 400. Based on this information, microcontroller 400 then initiates either a test strip sequence or a check strip sequence, as described above. Throughout either sequence, microcontroller 400 may periodically check the voltage, at contact 244 to make sure that the strip is still inserted in strip connector 216. Alternatively, an interrupt may notify microcontroller 400 of a voltage increase at contact 244 caused by removal of the strip.

In this way, the auto-on voltage drop developed across the auto-on conductor performs several functions in meter 200. First, the auto-on voltage wakes up meter 200 from a sleep mode to an active mode. Second, meter 200 determines the strip type from the magnitude of the auto-on voltage. Third, the auto-on voltage lets meter 200 know that the strip is still inserted in strip connector 216, as meter 200 proceeds with either the test strip or check strip sequence.

6. Conclusion

Preferred embodiments of the present invention have been described above. Those skilled in the art will understand, however, that changes and modifications may be made to these embodiments without departing from the true scope and spirit of the invention, which is defined by the claims.

The invention claimed is:

1. A method for making a plurality of test strips, comprising:
    forming an array of test strip structures on a first insulating sheet, each of the test strip structures including:
        a first conductive pattern disposed on the first insulating sheet, the first conductive pattern forming at least four electrodes including a working electrode, a counter electrode, a fill-detect cathode, and a fill-detect anode,
        a second conductive pattern disposed on the first insulating sheet spaced from the first conductive pattern, the second conductive pattern including a plurality of spaced electrical contacts, and
        a plurality of conductive traces disposed on the first insulating sheet for electrically connecting the first and second conductive patterns,
    attaching a second insulating sheet to the first insulating sheet, the second insulating sheet formed to include a slot defining a sample chamber in the test strip, the slot including a proximal end and a distal end;
    attaching a cover layer to the second insulating sheet with an adhesive layer, the adhesive layer including the break, the break extending from the distal end of the slot to an opening for venting the sample chamber, and the cover layer overlying the slot and the break; and
    separating the plurality of test strip structures into the plurality of test strips.

2. The method of claim 1, wherein the cover layer is transparent.

3. The method of claim 1, wherein the plurality of spaced electrical contacts are at least partially exposed nearest to a distal end of each of the test strip structures.

4. The method of claim 1, wherein the plurality of spaced electrical contacts include a working electrode contact, a counter electrode contact, a fill-detect cathode contact, and a fill-detect anode contact.

5. The method of claim 1, wherein the slot is disposed nearest to a proximal end of each of the test strip structures.

6. The method of claim 5, wherein the slot defining the sample chamber at least partially exposes the at least four electrodes.

7. The method of claim 1, wherein the plurality of conductive traces include a working electrode trace, a counter electrode trace, a fill-detect cathode trace, and a fill-detect anode trace.

8. The method of claim 7, wherein the working electrode trace electrically connects the working electrode to the working electrode contact.

9. The method of claim 7, wherein the counter electrode trace electrically connects the counter electrode to the counter electrode contact.

10. The method of claim 7, wherein the fill-detect cathode trace electrically connects the fill-detect cathode to the fill-detect cathode contact.

11. The method of claim 7, wherein the fill-detect anode trace electrically connects the fill-detect anode to the fill-detect anode contact.

12. The method of claim 1, wherein the first conductive pattern is disposed nearest to a proximal end of each of the test strip structures.

13. The method of claim 1, wherein the working electrode and the counter electrode are disposed in an interleaving manner nearest to a proximal end of each of the test strip structures.

14. The method of claim 1, wherein the plurality of test strips are separated by punching each of the test strip structures to form a plurality of tapered structures.

15. The method of claim 14, wherein the plurality of test strips are further separated by slitting the plurality of tapered test strip structures into the plurality of test strips.

16. A method for making a plurality of test strips, comprising:
forming an integrated laminated structure including an array of test strip structures, the plurality of test strip structures including:
at least four electrodes disposed on a base layer in the integrated structure, the electrodes including a working electrode, a counter electrode, a fill-detect cathode, and a fill-detect anode,
a plurality of electrical contacts disposed in spaced relation from the electrodes on the base layer,
a plurality of conductive traces disposed on the base layer for electrically connecting the at least four electrodes and the plurality of electrical contacts,
a spacer layer attached to the base layer, the spacer layer including a slot defining a sample chamber in the test strip, the slot including a proximal end and a distal end, and
a cover layer attached to the spacer layer with an adhesive layer, the adhesive layer including a break, the break extending from the distal end of the slot to an opening for venting the sample chamber, and the cover layer overlying the slot and the break, and
separating the plurality of test strip structures on the integrated structure into the plurality of test strips.

17. The method of claim 16, wherein the plurality of electrical contacts include a working electrode contact, a counter electrode contact, a fill-detect cathode contact, and a fill-detect anode contact.

18. The method of claim 17, wherein the plurality of electrical contacts are disposed nearest to a distal end of each of the test strip structures.

19. The method of claim 16, wherein the plurality of conductive traces include a working electrode trace, a counter electrode trace, a fill-detect cathode trace, and a fill-detect anode trace.

20. The method of claim 19, wherein the plurality of conductive traces are longitudinally disposed on each of the test strip structures.

21. The method of claim 16, wherein the at least four electrodes are disposed nearest to a proximal end of each of the test strip structures.

22. The method of claim 16, wherein the cover layer is transparent.

23. The method of claim 16, wherein the slot is disposed nearest to a proximal end of each of the test strip structures.

24. The method of claim 23, wherein the slot defining the sample chamber at least partially exposes the at least four electrodes.

25. The method of claim 16, wherein the plurality of test strips are separated by punching the test strip structures to form a plurality of tapered structures.

26. The method of claim 25, wherein the plurality of test strips are further separated by slitting the plurality of tapered test strip structures into the plurality of test strips.

27. A method for making a plurality of test strips, comprising:
forming an array of test strip structures on a first substrate having a first edge and a second edge, the plurality of test strip structures including:
a plurality of electrodes sequentially disposed on the first substrate on a first region relatively nearest to the first edge for each test strip structure, the plurality of electrodes including at least a working electrode, a counter electrode, a fill-detect cathode, and a fill-detect anode,
a plurality of electrical contacts disposed on the first substrate on a second region relatively nearest to the second edge for each test strip structure, and
a plurality of conductive traces on the first substrate electrically connecting the plurality of electrodes and the plurality of electrical contacts,
attaching a second substrate to the first substrate, the second substrate having a slot defining a sample chamber in each test strip structure, the slot including a proximal end and a distal end, and the second substrate having a third edge and a fourth edge aligned, respectively, with the first edge and the second edge of the first substrate, the fourth edge being spaced from the second edge to at least partially expose the second region for each test strip structure;
attaching a cover layer to the second substrate with an adhesive layer, the adhesive layer including a break, the break extending from the distal end of the slot to an opening for venting the sample chamber, the cover layer overlying the slot and the break for each test strip structure, and the cover layer having a fifth edge and a sixth edge, the sixth edge being spaced from the fourth edge of the second substrate; and
separating the plurality of test strip structures into the plurality of test strips by punching the test strip structures to form a plurality of tapered structures, and slitting the plurality of tapered test strip structures into the plurality of test strips.

28. The method of claim 27, wherein the plurality of electrical contacts include a working electrode contact, a counter electrode contact, a fill-detect cathode contact, and a fill-detect anode contact.

29. The method of claim 27, wherein the plurality of conductive traces include a working electrode trace, a counter electrode trace, a fill-detect cathode trace, and a fill-detect anode trace.

30. The method of claim 27, wherein the second substrate includes a slot defining a sample chamber in the test strip.

31. The method of claim 30, wherein the slot is disposed nearest to the third edge of each of the test strip structures.

32. The method of claim 31, wherein the slot defining the sample chamber at least partially exposes the plurality of electrodes.

33. The method of claim 27, wherein the cover layer is transparent.

34. The method of claim 27, wherein the plurality of electrical contacts are at least partially exposed nearest to the second edge of each of the test strip structures.

35. The method of claim 27, wherein the working electrode and the counter electrode are disposed in an interleaving manner nearest to the first edge of each of the test strip structures.

* * * * *